(12) United States Patent
Golec et al.

(10) Patent No.: US 7,906,650 B2
(45) Date of Patent: Mar. 15, 2011

(54) CASPASE INHIBITORS AND USES THEREOF

(75) Inventors: Julian M. C. Golec, Woolstone, Faringdon (GB); Paul S. Charifson, Framingham, MA (US); Jean-Damien Charrier, Abingdon (GB); Hayley Marie Binch, Encinitas, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/359,749

(22) Filed: Jan. 26, 2009

(65) Prior Publication Data

US 2009/0131456 A1    May 21, 2009

Related U.S. Application Data

(60) Division of application No. 10/166,437, filed on Jun. 10, 2002, now Pat. No. 7,517,987, which is a continuation of application No. PCT/US00/33260, filed on Dec. 8, 2000.

(60) Provisional application No. 60/169,812, filed on Dec. 8, 1999.

(51) Int. Cl.
    *C07D 215/38* (2006.01)
(52) U.S. Cl. ........................................ 546/159; 546/156
(58) Field of Classification Search .................. 546/153, 546/156, 159; 514/312
    See application file for complete search history.

(56) References Cited

U.S. PATENT DOCUMENTS 5,801,148 A * 9/1998 Gyorkos et al. ................ 514/18
7,517,987 B2 * 4/2009 Golec et al. .................... 546/153

FOREIGN PATENT DOCUMENTS

WO            9816502      *  4/1998

* cited by examiner

*Primary Examiner* — D. Margaret Seaman
(74) *Attorney, Agent, or Firm* — Jennifer G. Che; Lisa A. Dixon; Vertex Pharmaceuticals Incorporated

(57) ABSTRACT

This invention provides novel compounds, and pharmaceutically acceptable derivatives thereof, that are useful as caspase inhibitors. These compounds have the general formula I:

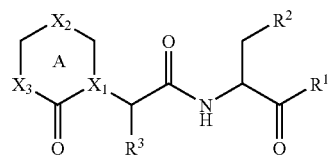

where $R^1$, $R^2$, and $R^3$ are as described herein, Ring A contains zero to two double bonds, each X is independently selected from nitrogen or carbon, at least one X in Ring A is a nitrogen, Ring A is optionally substituted as described, and may be fused to a saturated or unsaturated five to seven membered ring containing zero to three heteroatoms, and provided that when $X_3$ is a carbon, a substituent on $X_3$ is attached by an atom other than nitrogen.

8 Claims, No Drawings

CASPASE INHIBITORS AND USES THEREOF

CROSS-REFERENCE TO RELATED APPLICATIONS

This application is a divisional of U.S. patent application Ser. No. 10/166,437, filed Jun. 10, 2002, now U.S. Pat. No. 7,517,987 which is claims the benefit of International Application No. PCT/US00/33260, filed Dec. 8, 2000, which claims the benefit of U.S. Provisional Application No. 60/169,812, filed Dec. 8, 1999, the contents of which are incorporated herein by reference.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science,* 1998, 281, 1283-1312; Ellis et al., *Ann. Rev. Cell. Biol.,* 1991, 7, 663).

Caspases are a family of cysteine protease enzymes that are key mediators in the signaling pathways for apoptosis and cell disassembly (Thornberry, *Chem. Biol.,* 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, 5 and 13, have been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, 5 and 13. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon-γ inducing factor (IGIF) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$—[P4]-[P3]-[P2]-CH(R)$CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improved survival after endotoxic shock. Yaoita et al., *Circulation,* 97, 276 (1998); Endres et al., *J Cerebral Blood Flow and Metabolism,* 18, 238, (1998); Cheng et al., J. Clin. Invest., 101, 1992 (1998); Yakovlev et al., *J Neuroscience,* 17, 7415 (1997); Rodriquez et al., *J. Exp. Med.,* 184, 2067 (1996); Grobmyer et al., *Mol. Med.,* 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies,* Clark and Moos, Eds. (Ellis Horwood, Chichester, England, 1990).

Recognizing the need to improve the pharmacological properties of the peptidic caspase inhibitors, peptidomimetic inhibitors have been reported. Amongst these, inhibitors where the P3 amino acid has been replaced by derivatives of 3-aminopyridin-2-ones and 5-aminopyrimidin-4-ones have received much attention (U.S. Pat. No. 5,756,466 (Bemis et al.); Dolle et al. *J. Med. Chem.* 39, 2438, (1996); Golec et al. *Bioorg. Med. Chem. Lett.* 7, 2181, (1997); Semple et al, *Biorg. Med. Chem. Lett.* 7, 1337, (1997)) leading to compounds of general structure:

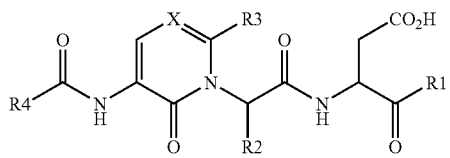

where $R^1$ is hydrogen or various groups, $R^2$ is hydrogen, methyl or ethyl, $R^3$ is alkyl, phenyl or phenalkyl, and $R^4$ is various groups.

Due to the inherent problems of the peptidic inhibitors, there continues to be a need for small molecule, nonpeptide caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are effective as inhibitors of caspases and cellular apoptosis. These compounds have the general formula I:

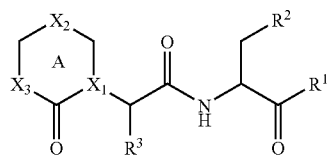

where $R^1$ is hydrogen, CN, $CHN_2$, R, or $-CH_2Y$;
R is an aliphatic group, a substituted aliphatic group, an aryl group, a substituted aryl group, an aralkyl group, a substituted aralkyl group, a non-aromatic heterocyclic group or a substituted non-aromatic heterocyclic group;
Y is an electronegative leaving group or $-OR$, $-SR$, $-OC=O(R)$, or $-OPO(R^8)(R^9)$;
$R^8$ and $R^9$ are independently selected from R or OR;
$R^2$ is $CO_2H$, $CH_2CO_2H$, or esters, amides or isosteres thereof;
$R^3$ is hydrogen or a $C_{1-6}$ straight chained or branched alkyl;
Ring A contains zero to two double bonds, and is optionally fused to a saturated or unsaturated five to seven membered ring containing zero to three heteroatoms;
$X_1$ and $X_3$ in Ring A are independently selected from nitrogen or carbon, and $X_2$ is selected from a valence bond, oxygen, sulfur, nitrogen or carbon, wherein any X with suitable valence may bear a substituent;
each carbon with suitable valence in Ring A, including the fused ring if present, is independently substituted by hydrogen, halo, R, OR, SR, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, $NHS(O)_2R$, $=O$, $=S$, $=NNHR$, $=NNR_2$, $=N-OR$, $=NNHCOR$, $=NNHCO_2R$, $=NNHSO_2R$, or $=NR$;
each substitutable nitrogen in Ring A is substituted by hydrogen, R. COR, $S(O)_2R$, or $CO_2R$;
provided that when $X_3$ is a carbon, a substituent on $X_3$ is attached by an atom other than nitrogen,
and further provided that at least one X in Ring A is a nitrogen.

The compounds of this invention have potent inhibition properties across a range of caspase targets with good efficacy in cellular models of apoptosis. In addition, these compounds are expected to have improved cell penetration and pharmacokinetic properties and, as a consequence of their potency, have improved efficacy against diseases where caspases are implicated.

DETAILED DESCRIPTION OF THE INVENTION

This invention provides novel compounds, and pharmaceutically acceptable derivatives thereof, that are useful as caspase inhibitors. These compounds have the general formula I:

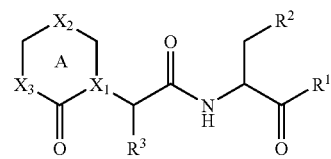

where $R^1$ is hydrogen, CN, $CHN_2$, R, or $-CH_2Y$;
R is an aliphatic group, a substituted aliphatic group, an aryl group, a substituted aryl group, an aralkyl group, a substituted aralkyl group, a non-aromatic heterocyclic group or a substituted non-aromatic heterocyclic group;
Y is an electronegative leaving group or $-OR$, $-SR$, $-OC=O(R)$, or $-OPO(R^8)(R^9)$;
$R^8$ and $R^9$ are independently selected from R or OR;
$R^2$ is $CO_2H$, $CH_2CO_2H$, or esters, amides or isosteres thereof;
$R^3$ is hydrogen or a $C_{1-6}$ straight chained or branched alkyl;
Ring A contains zero to two double bonds, and is optionally fused to a saturated or unsaturated five to seven membered ring containing zero to three heteroatoms;
$X_1$ and $X_3$ in Ring A are independently selected from nitrogen or carbon, and $X_2$ is selected from a valence bond, oxygen, sulfur, nitrogen or carbon, wherein any X with suitable valence may bear a substituent;
each carbon with suitable valence in Ring A, including the fused ring if present, is independently substituted by hydrogen, halo, R, OR, SR, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, S(O)R, $SO_2NHR$, $NHS(O)_2R$, $=O$, $=S$, $=NNHR$, $=NNR_2$, $=N-OR$, $=NNHCOR$, $=NNHCO_2R$, $=NNHSO_2R$, or $=NR$;
each substitutable nitrogen in Ring A is substituted by hydrogen, R. COR, $S(O)_2R$, or $CO_2R$;
provided that when $X_3$ is a carbon, a substituent on $X_3$ is attached by an atom other than nitrogen;
and further provided that at least one X in Ring A is a nitrogen.

As used herein, the following definitions shall apply unless otherwise indicated. The term "aliphatic" as used herein means straight chained, branched or cyclic $C_1$-$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl) alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O or S and shall include any oxidized form of nitrogen and sulfur, and the quaternized form of any basic nitrogen.

The term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 3-pyridazinyl, 2-thiazolyl, 4-thiazolyl, 5-thiazolyl, 5-tetrazolyl, 2-triazolyl, 5-triazolyl, 2-thienyl, or 3-thienyl.

Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclic ring, for example, indanyl or tetrahydrobenzopyranyl.

Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-1-alkyl-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane.

An aryl group (carbocyclic and heterocyclic) or an aralkyl group, such as benzyl or phenethyl, may contain one or more substituents. Examples of suitable substituents on the unsaturated carbon atom of an aryl group include a halogen, —R, —OR, —OH, —SH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, or —NHS(O)$_2$R, where R is an aliphatic group or a substituted aliphatic group.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon as well as the following: =O, =S, =NNHR, =NNR$_2$, =N—OR, =NNHCOR, =NNHCO$_2$R, =NNHSO$_2$R, or =NR.

A substitutable nitrogen on an aromatic or non-aromatic heterocyclic ring may be optionally substituted. Suitable substituents on the nitrogen include R, COR, S(O)$_2$R, and CO$_2$R, where R is an aliphatic group or a substituted aliphatic group.

The term "electronegative leaving group" has the definition known to those skilled in the art (see March, *Advanced Organic Chemistry*, 4$^{th}$ Edition, John Wiley & Sons, 1992). Examples of electronegative leaving groups include halogens such as F, Cl, Br, I, -aryl and alkylsulfonyloxy groups, trifluoromethanesulfonyloxy.

Isosteres or bioisosteres of carboxylic acids, esters and amides result from the exchange of an atom or group of atoms to create a new compound with similar biological properties to the parent carboxylic acid, ester or amide. The bioisosteric replacement may be physicochemically or topologically based. An example of an isosteric replacement for a carboxylic acid is CONHSO$_2$(alkyl) such as CONHSO$_2$Me.

Compounds of this invention where R$^2$ is COOH or CH$_2$COOH are gamma (y=1) or delta-ketoacids (y=2) which may exist in solution as either the open form 1 or the cyclized hemiketal form 2. The representation herein of either isomeric form is meant to include the other.

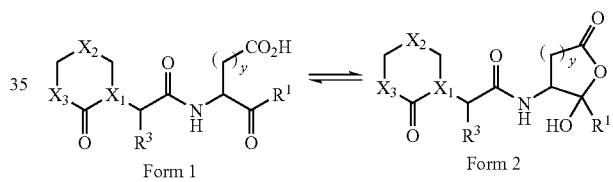

Form 1    Form 2

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Preferred compounds of this invention are those compounds of formula I where R$^2$ is CO$_2$H or ester, amide or isostere thereof. More preferred are those compounds of formula I where R$^2$ is CO$_2$H, or ester, amide or isostere thereof and X$_1$ is nitrogen.

One embodiment of this invention relates to compounds of formula I where X$_1$ is nitrogen, X$_2$ and X$_3$ are carbon, and Ring A has two double bonds. These compounds are represented by formula IA:

IA

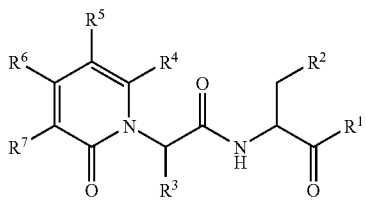

where R¹ is hydrogen, CN, CHN₂, R, or —CH₂Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or —OR, —SR, —OC=O(R), or —OPO(R⁸)(R⁹);

R⁸ and R⁹ are independently selected from R or OR;

R² is CO₂H, CH₂CO₂H, or esters, amides or isosteres thereof;

R³ is hydrogen or a C₁₋₆ straight chained or branched alkyl;

each of s is independently selected from hydrogen, halo, R, OR, SR, aryl, substituted aryl, OH, NO₂, CN, NH₂, NHR, N(R)₂, NHCOR, NHCONHR, NHCON(R)₂, NRCOR, NHCO₂R, CO₂R, CO₂H, COR, CONHR, CON(R)₂, S(O)₂R, SONH₂, S(O)R, SO₂NHR, or NHS(O)₂R;

R⁷ is selected from hydrogen, halo, R, OR, SR, aryl, substituted aryl, OH, CN, CO₂R, CO₂H, COR, CONHR, CON(R)₂, S(O)₂R, SONH₂, S(O)R, or SO₂NHR.

Preferred compounds of formula IA are those compounds where R¹ is CH₂F, R² is CO₂H, R³ is H or methyl, R⁴-R⁶ is independently selected from hydrogen, R, phenyl or substituted phenyl, and R⁷ is hydrogen, R, phenyl or substituted phenyl. Examples of IA compounds are shown in Table 1.

TABLE 1

Examples of Formula IA Compounds

| Number | R¹ | R² | R³ | R⁴ | R⁵ | R⁶ | R⁷ |
|---|---|---|---|---|---|---|---|
| 1A-1 | CH₂F | CO₂H | H | H | H | H | H |
| 1A-2 | CH₂F | CO₂H | Me | H | H | H | H |
| 1A-3 | CH₂F | CO₂H | H | Me | H | H | H |
| 1A-4 | CH₂F | CO₂H | H | H | H | Ph | H |
| 1A-5 | CH₂F | CO₂H | H | H | H | H | Ph |
| 1A-6 | CH₂F | CO₂H | H | Et | H | H | Ph |

Another embodiment of this invention relates to compounds of formula I where X₁ is nitrogen, X₂ and X₃ are carbon, Ring A has two double bonds, and R⁴ and R⁵ taken together form a fused, aromatic or non-aromatic carbocyclic ring. Preferably the carbocyclic ring is a fused benzene ring. Such preferred compounds have the general formula IB, where R¹, R², R³, R⁶ and R⁷ are as described above and the fused benzene ring may be substituted or unsubstituted. Examples of 1B compounds are shown in Table 2.

TABLE 2

Examples of Formula IB Compounds

IB

| Number | R¹ | R² | R³ | R⁶ | R⁷ |
|---|---|---|---|---|---|
| 1B-1 | CH₂F | CO₂H | Me | H | H |
| 1B-2 | CH₂F | CO₂H | H | H | H |

Another embodiment of this invention relates to compounds of formula I where X₁ is nitrogen, X₂ is nitrogen or carbon, X₃ is carbon, the bond between X₂ and the adjacent CR⁴ is either a double or single bond, and R⁶ and R taken together form a fused, aromatic or non-aromatic carbocyclic ring. Preferably, the carbocyclic ring is a fused benzene ring. Such preferred compounds have the general formula IC, where R¹-R⁵ are as described above, and the fused benzene ring may be substituted or unsubstituted. Examples of IC compounds are shown in Table 3.

TABLE 3

Examples of Formula IC Compounds

IC

| No. | R¹ | R² | R³ | R⁴ | R⁵ | X² | Bond order X²—CR⁴ |
|---|---|---|---|---|---|---|---|
| 1C-1 | CH₂F | CO₂H | H | H | H | C | Double |
| 1C-2 | CH₂F | CO₂H | Me | H | H | C | Double |
| 1C-3 | CH₂F | CO₂H | H | H | — | N | Double |
| 1C-4 | CH₂F | CO₂H | H | H₂ | H₂ | C | Single |
| 1C-5 | CH₂OAr | CO₂H | Me | H | H | C | Double |
| 1C-6 | CH₂F | CO₂H | Me | H | — | N | Double |
| 1C-7 | CH₂OAr | CO₂H | Me | H | — | N | Double |
| 1C-8 | CH₂F | CO₂H | Et | H | — | N | Double |
| 1C-9 | CH₂F | CO₂H | Et | H | — | N | Double |
| 1C-10 | CH₂F | CO₂H | iPr | H | — | N | Double |
| IC-11 | CH₂F | CO₂H | Pr | H | — | N | Double |
| 1C-12 | H | CO₂H | Et | H | — | N | Double |

Another embodiment of this invention relates to compounds of formula I where $X_1$ and $X_3$ are nitrogen, $X_2$ is carbon, Ring A has one double bonds and $R^5$ and $R^6$ taken together form a ring, preferentially an aromatic carbocyclic ring. These compounds have the general formula ID shown below, where $R^1$-$R^4$ and $R^7$ are as described above. Examples of ID compounds are shown in Table 4.

TABLE 4

Examples of Formula ID Compounds

ID

| No. | $R^1$ | $R^2$ | $R^3$ | $R^4$ | $R^7$ |
|-----|-------|-------|-------|-------|-------|
| 1D-1 | $CH_2F$ | $CO_2H$ | iPr | $H_2$ | 3-ClPhCH$_2$ |

Another embodiment of this invention relates to compounds of formula I where $X_1$ is nitrogen, $X_2$ is nitrogen or carbon, $X_3$ is carbon, the bond between $X_2$ and the adjacent $CR^4$ is either a double or single bond, and $R^6$ and $R^7$ taken together form a fused, aromatic or non-aromatic heterocyclic ring. These compounds have the general formula IE, where $R^1$-$R^5$ are as described above, and the fused heterocyclic ring may be substituted or unsubstituted. Preferably, the heterocyclic ring is a five or six membered ring having one ring heteroatom. These compounds have the general formula IE shown below. Examples of IE compounds are shown in Table 5.

TABLE 5

Examples of IE Compounds ($R^1$ is $CH_2F$; $R^2$ is $CO_2H$)

IE

| No. | Heterocycle | $R^3$ | $R^4$ | $R^5$ | $X_2$ | Bond order $X^2$—$CR^4$ |
|-----|-------------|-------|-------|-------|-------|-------------------------|
| IE-1 | Thiophene[2,3-d] | H | H | — | N | double |
| IE-2 | Pyridine[4,3-d] | H | H | H | C | double |

Another embodiment of this invention relates to compounds of formula I where $X_1$ is nitrogen, $X_2$ is a bond, $X_3$ is carbon, and $R^6$ and $R^7$ taken together form a fused, aromatic or non-aromatic heterocyclic ring. These compounds have the general formula IF, where $R^1$-$R^5$ are as described above, and the fused ring may be substituted or unsubstituted. Preferably, the fused ring is a six membered ring. These compounds have the general formula IF shown below. Examples of IF compounds are shown in Table 6.

TABLE 6

Examples of IF Compounds

IF

| No. | $R^1$ | $R^2$ | $R^3$ | $R^4$ |
|-----|-------|-------|-------|-------|
| IF-1 | $CH_2F$ | $CO_2H$ | H | $H_2$ |
| IF-2 | $CH_2F$ | $CO_2H$ | Me | =O |
| IF-3 | $CH_2F$ | $CO_2H$ | Me | $H_2$ |

Another embodiment of this invention relates to compounds of formula I where $X_1$ is nitrogen, $X_2$ is nitrogen, $X_3$ is carbon, and Ring A has two double bonds. These compounds have the general formula IG, where $R^1$-$R^7$ are as described above. These compounds have the general formula IG shown below. Examples of IG compounds are shown in Table 7.

TABLE 7

Examples of IG compounds

IG

| No. | $R^1$ | $R^2$ | $R^3$ | $R^4$ | $R^6$ | $R^7$ |
|-----|-------|-------|-------|-------|-------|-------|
| IG-1 | $CH_2F$ | $CO_2H$ | Et | H | H | H |

The compounds of this invention may be prepared in general by methods known to those skilled in the art for analogous compounds, as illustrated by the general Schemes below and by the preparative examples that follow.

Scheme I

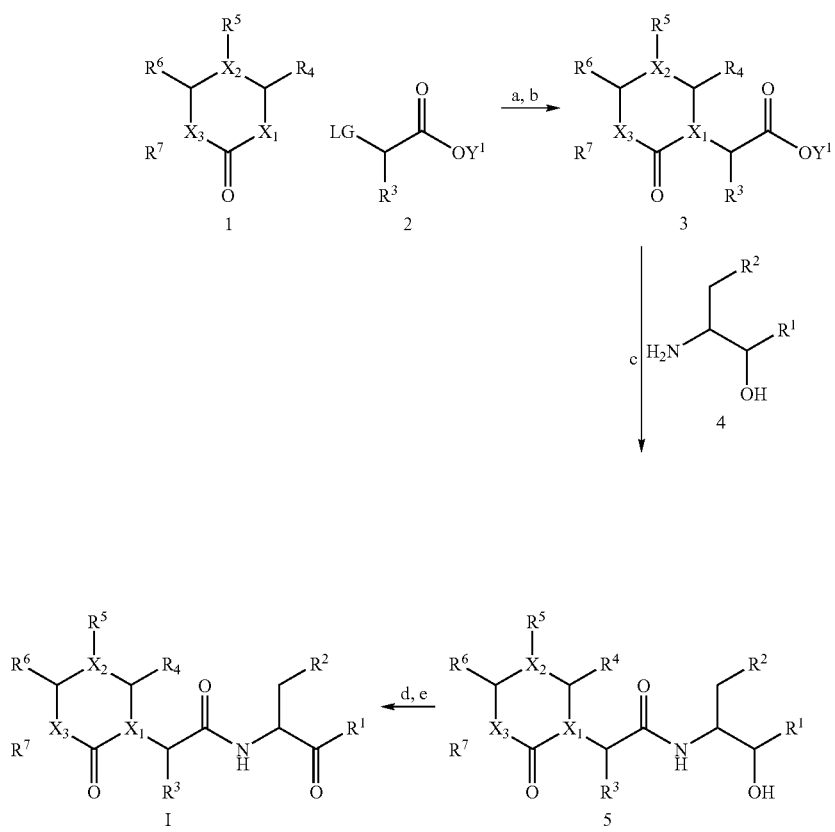

Reagents: (a) NaH/THF; (b) NaOH/THF/H₂O; (c) EDC/DMAP/HOBt; (d) Dess-Martin periodinane; (e) TFA/DCM In Scheme I above, the following abbreviations are used: EDC is 1-(3-dimethylaminopropyl)-3-ethylcarbodiimide; HOBT is 1-hydroxybenzotriazole; TFA is trifluoroacetic acid; DCM is dichloromethane; and DMAP is 4-dimethylaminopyridine. The starting heterocycle 1, is either commercially available or prepared by methods analogous to those described by Fuss and Koch, *Synthesis* (1990), 681-685, unless stated otherwise. Starting heterocycle 1 is treated first with sodium hydride, then with an ester 2 (LG is a leaving group such as bromine or O-triflate). The resulting ester 3 (e.g., $Y^1$=alkyl) is first hydrolized using base or, when $Y^1$ is a t-butyl group, using trifluoroacetic acid. The acid 3 ($Y^1$=H) is then coupled with the amino alcohol 4. Depending on the nature of $R^1$ and $R^2$ an amino ketone may be used, in place of the amino alcohol, which avoids the subsequent oxidation step. In the case of fluoromethyl ketones where $R^1$ is $CH_2F$, the amino alcohol 4 may be obtained according to the method of Revesz et al., *Tetrahedron Lett.*, 1994, 35, 9693. Finally the hydroxyl in compound 5 is oxidized and the compound treated appropriately according to the nature of $R^2$. For example, if the product I requires $R^2$ to be a carboxylic acid, then R in 4 is preferably an ester and the final step in the scheme is hydrolysis.

Accordingly, one aspect of this invention relates to a general method of preparing compounds of formula I comprising the steps of:

(a) providing an acid or acid derivative of formula II:

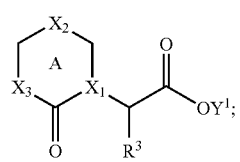

II (b) coupling II with an amino alcohol or amino ketone of formula 4 to provide an intermediate of formula III:

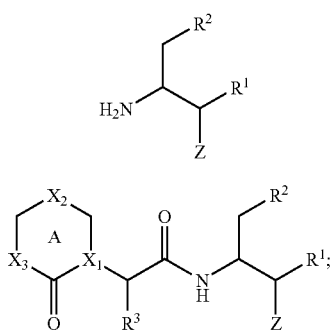

4

III and (c) converting intermediate III to compound I, wherein $Y^1$ is hydrogen or an organic radical; Z is =O or OH; and ring A, $R^1$, $R^2$, $R^3$, $X_1$, $X_2$ and $X_3$ are as described above.

This method is particularly useful for preparing chiral compounds of this invention, where the carbon bearing the $R^3$ substituent is stereochemically enriched. As exemplified below (see Examples 21-27), intermediate acids or acid derivatives of formula II may be obtained in chiral form. This is illustrated herein for Ring A being a quinazolin-4-one (Examples 21-24, 26), a pyrimidin-4-one (Example 25) and a dihydroquinazoline-3-one (Example 27). The step (b) coupling of II and 4 to provide III may be carried out according to any suitable method. It is understood that when 4 is a ketone (Z=O), it may need to be generated in the presence of II, for example, by in situ deprotection of the amino group. In step (c), the conversion of III to provide I will depend on the nature of Z and $R^2$. Synthetic manipulation of these groups, if necessary, may be performed as described herein or according to other methods familiar to those skilled in the art.

Certain chiral intermediates II, useful for making compounds of this invention, are novel. These intermediates are represented by pyrimidinones IIA and quinazolinones IIB:

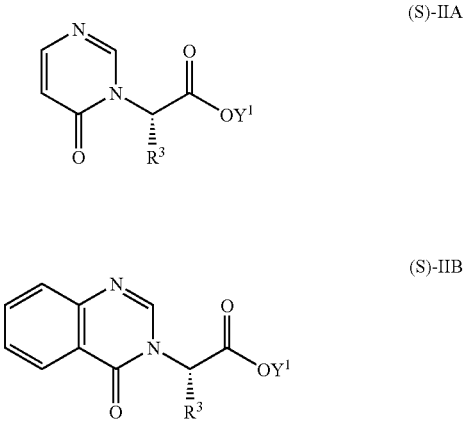

wherein $Y^1$ is hydrogen or an organic radical, the pyrimidinone and quinazolinone rings are optionally substituted as described above for Ring A, and $R^3$ is a $C_{1-6}$ alkyl group.

Scheme II

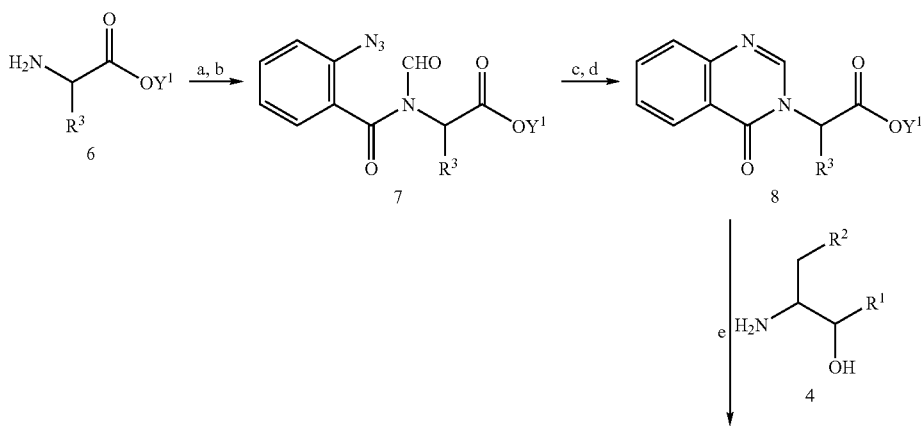

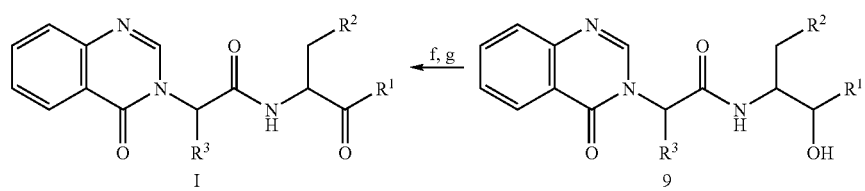

Reagents: (a) Ethyl formate/diisopropylamine; (b) ArCOCl/THF; (c) PPh$_3$/xylene; (d) TFA/DCM; (e) EDC/DMAP/HOBt; (f) Dess-Martin periodinane; (g) TFA/DCM In Scheme II above, the starting amino acid ester 6, which is commercially available or synthesised under standard conditions, is first formylated and then treated with an 2-azido aromatic acid, activated for example as an acid chloride. The resulting amide 7, is treated with a reducing agent such as triphenyl phosphine and the resulting ester (e.g., $Y^1$=alkyl) is hydrolized using base or, when $Y^1$ is a t-butyl group, using trifluoroacetic acid. The synthesis is then completed as outlined in Scheme I.

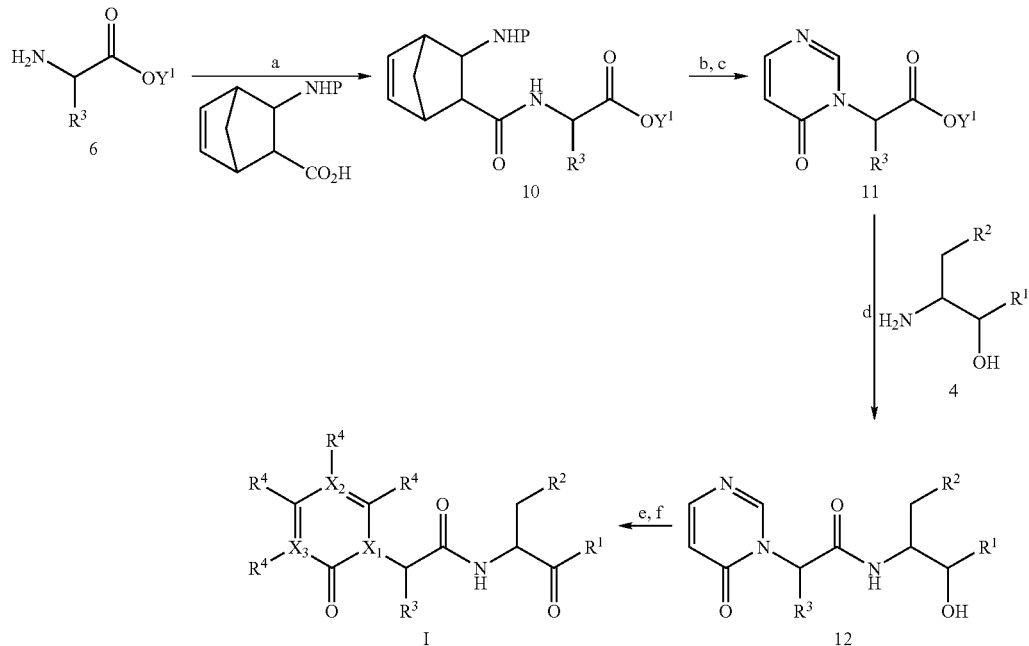

Reagents: (a) EDC/DMAP/HOBt; (b) HCl/EtOAc; (c) (EtO)$_3$CH/xylene; (d) EDC/DMAP/HOBt; (e) Dess-Martin periodinane; (f) TFA/DCM In Scheme III above, the starting amino acid ester 6, which is commercially available or synthesised under known methods, is coupled with an unsaturated amino acid under standard conditions to provide amide 10. The amide 10 is deprotected (e.g., P=Boc) using acid conditions and the resulting amine heated with a formylating agent, eg triethylorthoformate. The intermediate then undergoes a thermal retro-Diels Alder reaction to provide 11. The synthesis is then completed as outlined in Scheme I.

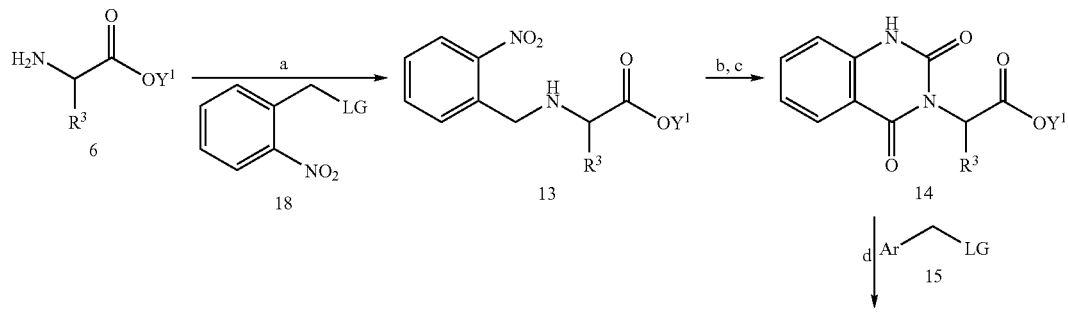

-continued

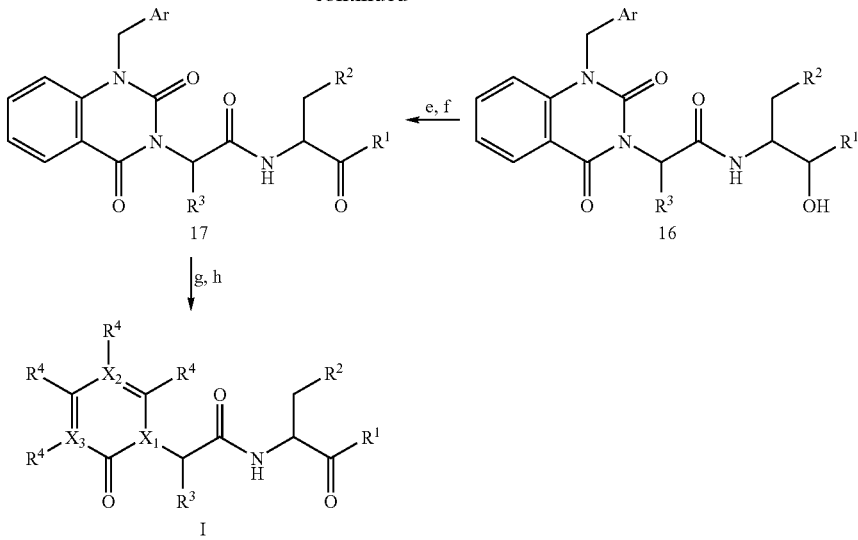

Reagents: (a) Et₃N/EtOH/18; (b) RaNi/H₂/EtOH; (c) CDI/THF; (d) NaH/DMSO/15; (e) TFA/DCM; (f) 4/EDC/DMAP/HOBt; (g) Dess-Martin periodinane; (h) TFA/DCM In Scheme IV above, the starting amino acid ester 6 is alkylated with a benzyl group (where LG may be a halogen, tosylate, mesylate, triflate or the like) to provide 13. The nitro group in 13 is reduced (for example with Raney Nickel) and the diamine then cyclized onto a carbonyl source, (e.g. carbonyl diimidazole, "CDI") to provide quinazolone 14. The resulting free NH may be alkylated to provide compound 16. The synthesis is then completed as outlined in Scheme I.

Example 1

5-Fluoro-4-oxo-3-[(S)-2-(2-oxo-2H-pyridin-1-yl)-propionylamino]-pentanoic acid (1A-2)

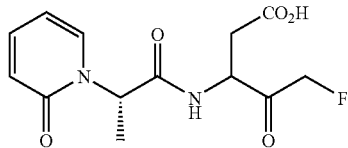

Step A: (S)-2-(2-Oxo-2H-pyrid-1-yl)-propionic acid ethyl ester. A stirred solution of 1H-Pyridin-2-one (500 mg, 5.26 mmol) in anhydrous THF (50 ml) at room temperature was treated portionwise with 60% NaH (231 mg, 5.78 mmol). The reaction mixture was kept for 10 min then added over 5 min to a solution of (R)-2-trifluoromethanesulfonyloxy)-propionic acid ethyl ester (1315 mg, 5.26 mmol) in anhydrous THF (2.5 ml) at room temperature. The resulting mixture was stirred for 2 h, then concentrated. The residue was dissolved in ethyl acetate, and the resulting solution was washed with ice cold dilute HCl. The organic layer was removed and the aqueous layer re-extracted with ethyl acetate. The combined organic extracts were dried (MgSO₄), filtered and concentrated. The residue was purified by flash chromatography (20% up to 80% ethyl acetate in hexane) to afford the title compound as a yellow oil (480 mg, 46%): $[\alpha]^{27}_D=-56.4°$ (c=0.275, CH₂Cl₂); ¹H NMR (400 MHz CDCl₃) δ 1.3 (3H, t), 1.65 (3H, d), 4.2 (2H, q), 5.6 (1H, q), 6.2 (1H, t), 6.4 (1H, d), 7.2-7.3 (2H, m).

Step B: (S)-2-(2-Oxo-2H-pyridin-1-yl)-propionic acid

A stirred mixture of (S)-2-(2-Oxo-2H-pyrid-1-yl)-propionic acid ethyl ester (364 mg, 1.87 mmol), THF (2 ml), water (1 ml) and sodium hydroxide (90 mg, 2.24 mmol) was kept at room temperature for 1 h, then concentrated under reduced pressure. The residue was dissolved in ether and the resulting solution washed with water. The organic layer was discarded and the aqueous layer was acidified with concentrated HCl then extracted several times with ethyl acetate. The combined organic extracts were dried (MgSO₄), filtered and concentrated. The residue was triturated with ether to afford the title compound as a colorless solid (84 mg, 27%): $[\alpha]^{31}_D=-50°$ (c=0.2, CH₃OH); ¹H NMR (400 MHz, DMSO) δ 1.5 (3H, d), 5.1 (1H, q), 6.2 (1H, t), 6.4 (1H, d), 7.4 (1H, m), 7.6 (1H, d).

Step C: 5-Fluoro-4-hydroxy-3-[(S)-2-(2-oxo-2H-pyridin-1-yl)-propionylamino]-pentanoic acid tert-butyl ester A stirred mixture of (S)-2-(2-Oxo-2H-pyridin-1-yl)-propionic acid (70 mg, 0.42 mmol), 3-Amino-5-fluoro-4-hydroxy-pentanoic acid tert-butyl ester (91 mg, 0.44 mmol), HOAt (63 mg, 0.46 mmol) and DMAP (59 mg, 0.48 mmol) and anhydrous THF (5 ml) was cooled to 0° C. then EDC (88 mg, 0.46 mmol) was added. The mixture was allowed to warm to room temperature during 16 h then concentrated under reduced pressure. The residue was purified by flash chromatography (3% methanol in ethyl acetate) to afford the title compound as a white foam (137 mg, 92%): ¹H NMR (400 MHz, CDCl₃) δ 1.3-1.5 (9H, 2×s), 2.5-2.7 (2H, m), 3.4-3.7 (1H, m), 3.9-4.6 (4H, m), 5.4-5.6 (1H, m), 6.2-6.3 (1H, m), 6.5-6.6 (1H, m), 7.1-7.6 (3H, m); ¹⁹F NMR (376 MHz, CDCl₃) δ −230.14, −230.14, −230.17, −230.95, −231.07.

Step D: 5-Fluoro-4-oxo-3-[(S)-2-(2-oxo-2H-pyridin-1-yl)-propionylamino]-pentanoic acid tert-butyl ester A stirred solution of 5-Fluoro-4-hydroxy-3-[(S)-2-(2-oxo-2H-pyridin-1-yl)-propionylamino]-pentanoic acid tert-butyl ester (135 mg, 0.38 mmol) in anhydrous DCM (5 ml) was treated with 1,1,1-triacetoxy-1,1-dihydro-1,2-benziodoxol-3 (1H)-one (193 mg, 0.46 mmol) at 0° C. The resulting mixture was kept at 0° C. for 1.5 h, diluted with ethyl acetate, then poured into a 1:1 mixture of saturated aqueous sodium hydrogen carbonate and saturated aqueous sodium thiosulphate. The organic layer was removed and the aqueous layer re-extracted with ethyl acetate. The combined organic extracts were dried ($Na_2SO_4$) and concentrated. The residue was purified by flash chromatography (1% methanol in ethyl acetate) to afford the title compound as a colorless gum (125 mg, 93%): $^1$H NMR (400 MHz, $CDCl_3$) δ 1.2-1.4 (9H, 2×s), 2.6-2.9 (2H, m), 4.7-4.9 (1H, m), 4.9-5.3 (2H, m), 5.6-5.7 (1H, m), 6.2-6.3 (1H, m), 6.5-6.6 (1H, m), 7.2-7.4 (1H, m), 7.5-7.6 (1H, m), 8.0-8.2 (1H, m); $^{13}$C NMR (100 MHz, $CDCl_3$) δ 16.57, 16.87, 28.24, 28.29, 36.44, 36.60, 52.50, 52.62, 52.90, 53.09, 82.31, 82.44, 83.51, 83.72, 85.33, 85.55, 107.35, 107.44, 120.45, 120.49, 134.42, 134.67, 140.22, 140.36, 162.85, 162.98, 169.93, 169.99, 170.59, 170.63, 202.58, 202.64, 202.75, 202.80; $^{19}$F NMR (376 MHz, $CDCl_3$) δ −231.94, −231.96, −232.48, −232.49.

Step E: 5-Fluoro-4-oxo-3-[(S)-2-(2-oxo-2H-pyridin-1-yl)-propionylamino]-pentanoic acid Trifluoroacetic acid (2 ml) was added to a stirred ice cold solution of 5-Fluoro-4-oxo-3-[(S)-2-(2-oxo-2H-pyridin-1-yl)-propionylamino]-pentanoic acid tert-butyl ester (115 mg, 0.32 mmol) in anhydrous dichloromethane (2 ml). The mixture was stirred at 0° C. for 0.5 h then at room temperature for 0.5 h. The mixture was concentrated under reduced pressure and then the residue was redissolved in dry dichloromethane. This process was repeated several times in order to remove excess trifluoroacetic acid. The gum was lyophilized twice from HPLC grade water to afford the title compound as an off white solid: IR (solid) 1789, 1730, 1654 cm$^{-1}$; $^1$H NMR (400 MHz, DMSO) δ 1.4-1.6 (3H, m), 2.5-2.9 (2H, m), 4.2-4.7 (2H, m), 5.0-5.5 (2H, m), 6.2-6.3 (1H, m), 6.3-6.5 (1H, m), 7.3-7.4 (1H, m), 7.6-7.7 (1H, m), 8.4-8.9 (1H, m); $^{13}$C NMR (100 MHz, DMSO) δ 17.15, 17.27, 17.61, 17.87, 17.94, 33.50, 33.57, 35.02, 35.23, 35.31, 52.69, 53.08, 53.31, 53.42, 53.47, 53.79, 53.91, 54.49, 54.85, 81.55, 81.92, 83.31, 83.68, 83.95, 84.07, 85.72, 85.84, 105.87, 106.07, 106.19, 119.67, 119.86, 120.26, 137.05, 137.31, 137.36, 137.40, 137.43, 140.60, 140.65, 140.74, 140.85, 162.14, 162.18, 162.28, 162.32, 171.25, 171.48, 171.62, 171.69, 172.55, 172.63, 173.63, 173.67, 174.52, 203.04, 203.18, 203.28, 203.42; MS (FAB +ve, HR) Calculated for $C_{13}H_{16}FN_2O_5$ (MH+) 299.1043. found 299.1045.

Example 2

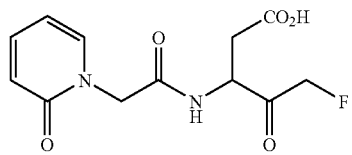

5-Fluoro-3-[2-(2-oxo-2H-pyridin-1-yl)-acetylamino]-4-oxo-pentanoic acid (1A-1) was prepared in a manner similar to that described in Example 1 except that in step A (R)-2-trifluoromethanesulfonyloxy)-propionic acid ethyl ester is replaced by bromoacetic acid ethyl ester. The product was isolated as a yellow solid: IR (solid) 1657.5, 1694.3, 1781.3 cm$^{-1}$; $^1$H NMR (400 MHz, DMSO) δ 2.5-2.9 (2H, m), 4.3-4.7 (3.5H, m), 5.1-5.5 (1.5H, m), 6.2 (1H, m), 6.3-6.4 (1H, m), 7.4 (1H, m), 7.6 (1H, m), 8.5-9.0 (1H, m); $^{13}$C NMR (100 MHz, DMSO) δ (DMSO) 28.71, 33.17, 51.13, 51.64, 51.70, 52.25, 52.91, 80.96, 81.74, 82.72, 83.46, 83.59, 85.35, 105.16, 105.23, 105.31, 119.54, 140.71, 140.82, 140.89, 161.82, 161.87, 161.94, 167.62, 167.73, 168.18, 172.12, 173.14, 173.80, 202.76, 202.89; $^{19}$F (376 MHz, DMSO) δ −226.9 (t), −231.8 (t), −233.3 (t).

Example 3

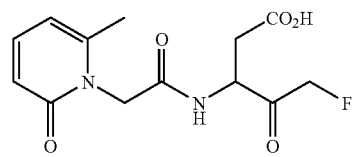

5-Fluoro-3-[2-(6-methyl-2-oxo-2H-pyridin-1-yl)-acetylamino]-4-oxo-pentanoic acid (1A-3) was prepared in a manner similar to that described in Example 2 to provide colorless crystals: IR (solid) 3276, 1741, 1716, 1669, 1642, 1548, 1414, 1377, 1352, 1273, 1248, 1227, 1189, 1163, 1043, 796 cm$^{-1}$; $^1$H NMR (400 MHz, DMSO) δ 2.25 (3H, s), 2.55-2.95 (2H, m), 4.3-4.8 (3H, m), 5.1-5.35 (2H, m), 6.06 (1H, m), 6.22 (1H, m), 7.27 (1H, m), 8.51, 8.82 (1H, 2×d); $^{13}$C NMR (100 MHz, DMSO) δ 20.83, 34.83, 46.47, 52.15, 83.52, 85.29, 103.82, 116.32, 139.97, 162.8, 167.8, 172.0, 173.1, 202.86.

Example 4

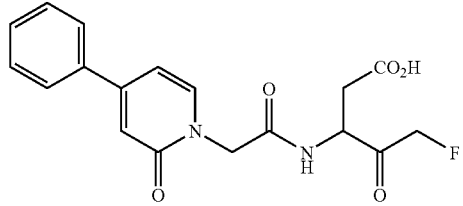

5-Fluoro-3-[2-(4-phenyl-2-oxo-2H-pyridin-1-yl)-acetylamino]-4-oxo-pentanoic acid (1A-4) was prepared from 4-phenylpyrimin-2-one (Iwasaki et al, *J. Med. Chem.* 1996, 39, 2696) in a manner similar to that described in Example 2 to provide a colorless solid: IR (solid) 3307.5, 3216.5, 1787.8, 1659.7, 1582.9, 1567.6, 1219.4, 1055.5, 927.5, 763.6 cm$^{-1}$; $^1$H NMR (400 MHz, DMSO) δ 2.66 (1H, m), 2.85 (1H, m), 4.31-4.72 (3H, m), 5.28 (2H, m), 6.59 (1H, m), 6.69 (1H, m), 7.51 (3H, m), 7.70 (3H, m), 8.50-8.95 (1H, br); $^{13}$C NMR (100 MHz, DMSO) δ 33.2, 34.7, 47.6, 50.8, 51.4, 52.3, 83.6, 85.4, 103.8, 104.0, 104.2, 104.3, 115.3, 127.0, 129.4, 129.9, 137.1, 140.7, 151.4, 151.6, 161.9, 162.0, 167.8, 168.2, 172.1, 173.1, 202.7, 202.9; $^{19}$F (376 MHz, DMSO) δ -226.8 (t), -231.8 (t), -233.27 (t).

Example 5

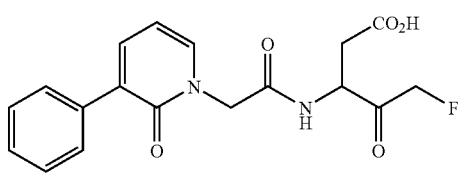

5-Fluoro-3-[2-(3-phenyl-2-oxo-2H-pyridin-1-yl)-acetylamino]-4-oxo-pentanoic acid (1A-5) was prepared from 3-phenylpyrimin-2-one. 3-Phenylpyrimin-2-one was prepared by bromination of pyrimidin-2-one (Oswald and Martinu *J. Am. Chem. Soc.*, 1982, 104, 4142), followed by palladium mediated coupling with benzene boronic acid according to a procedure described by Damewood et al. (*J. Med. Chem.*, 1994, 37, 3303). The rest of the synthesis was completed in a manner similar to that described in Example 2 to provide a colorless solid: IR (solid) 3392.3, 2941.1, 1745.4, 1673.9, 1635.4, 1564.0, 1396.3, 1236.2, 1203.4, 775.5, 700.9 cm$^{-1}$; $^1$H NMR (400 MHz, DMSO) δ 2.64 (1H, m), 2.79 (1H, m), 4.21-4.81 (3H, m), 5.29 (2H, m), 6.37 (1H, m), 7.28-7.41 (3H, m), 7.62-7.25 (4H, m), 8.2-8.9 (1H, brm); $^{13}$C NMR (100 MHz, DMSO) δ 32.2, 34.8, 47.6, 51.9, 52.2, 52.3, 80.9, 82.7, 83.6, 85.4, 103.8, 104.0, 105.4, 105.5, 105.6, 127.6, 127.7, 128.2, 129.6, 137.0, 137.1, 137.2, 138.6, 138.8, 139.5, 140.1, 158.4, 160.8, 160.9, 162.7, 167.7, 168.2, 169.9, 172.1, 173.1, 202.7, 202.9; $^{19}$F (376 MHz, DMSO) δ -226.8 (t), -231.6 (t), -233.2 (t).

Example 6

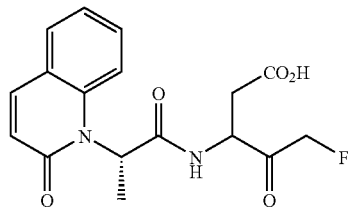

5-Fluoro-4-oxo-3-[(S)-2-(2-oxo-2H-quinolin-1-yl)-propionylamino]-pentanoic acid (1B-1) was prepared in a manner similar to that described in Example 1 to provide a white powder: IR (solid) 1782, 1737, 1641 cm$^{-1}$; $^1$H NMR (400 MHz, DMSO) δ 1.5 (3H, m), 2.3-2.4 (0.5H, m), 2.6-3.1 (1.5H, m), 4.2-4.8 (1.6H, m), 5.0-5.5 (1.4H, m), 5.5-6.0 (1H, br s), 6.6 (1H, m), 7.3 (1H, m), 7.3-7.7 (2H, br m), 7.7-7.8 (1H, m), 7.9-8.0 (1H, m), 8.2-8.5 (1H, br m); $^{13}$C NMR (100 MHz, DMSO) δ 14.06, 14.13, 14.25, 14.39, 32.77, 32.85, 34.29, 34.43, 51.75, 51.99, 52.30, 53.05, 83.41, 83.49, 85.17, 85.26, 114.56, 114.94, 115.13, 115.38, 120.95, 121.43, 121.35, 121.61, 122.34, 122.42, 122.48, 129.53, 129.59, 129.65, 130.66, 130.84, 130.91, 130.95, 131.18, 140.24, 140.32, 158.36, 158.70, 160.98, 161.41, 161.47, 167.71, 170.38, 171.86, 172.14, 172.16, 173.26, 202.35, 202.49, 202.53, 202.66; MS (FAB +ve, HR) Calculated for C$_{17}$H$_{18}$FN$_2$O$_5$ (MH+) 349.1200. found 349.1206.

Example 7

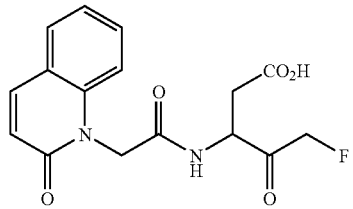

5-Fluoro-4-oxo-3-[(S)—(R)-2-(2-oxo-2H-quinolin-1-yl)-acetylamino]-pentanoic acid (1B-2) was prepared in a manner similar to that described in Example 2 to provide a white powder: IR (solid) 1784, 1738, 1703, 1638 cm$^{-1}$; $^1$H NMR (400 MHz, DMSO) δ 2.5-3.2 (2H, m), 4.3-4.7 (1.3H, m), 4.8-5.4 (3.7H, m), 6.6 (1H, m), 7.2-7.3 (2H, m), 7.5-7.6 (1H, m), 7.7-7.8 (1H, m), 7.9-8.0 (1H, m), 8.5-9.0 (1H, m); $^{13}$C NMR (100 MHz, DMSO) δ 33.25, 34.90, 44.51, 44.64, 44.74, 47.71, 52.81, 81.22, 81.59, 82.98, 83.32, 83.51, 85.28, 114.80, 120.48, 120.53, 120.97, 121.09, 122.36, 122.41, 129.24, 131.02, 131.06, 131.21, 139.92, 139.99, 140.27, 140.34, 140.48, 161.48, 161.56, 167.54, 167.74, 168.09, 172.08, 173.13, 173.93, 202.59, 202.73; MS (FAB +ve, HR) Calculated for C$_{16}$H$_{16}$FN$_2$O$_5$ (MH+) 335.1043. found 335.1046.

Example 8

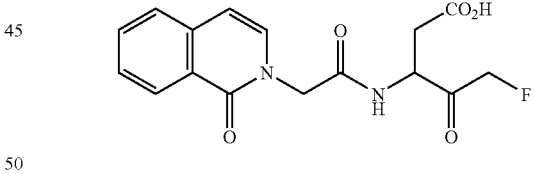

5-Fluoro-4-oxo-3-[2-(1-oxo-1H-isoquinolin-2-yl)-acetylamino]-pentanoic acid (1C-1) was prepared in a manner similar to that described in Example 2 to provide a white powder: IR (solid) 1778, 1738, 1688, 1646 cm$^{-1}$; $^1$H NMR (400 MHZ, DMSO) δ 2.6-3.2 (2H, m), 4.3-4.7 (3H, m), 5.1-5.4 (2H, m), 6.6 (1H, m), 7.4-7.6 (2H, m), 7.6-7.8 (2H, m), 8.2 (1H, m), 8.4-8.9 (1H, m); $^{13}$C NMR (100 MHz, DMSO) δ 33.20, 34.85, 51.01, 51.40, 47.59, 52.19, 52.91, 81.03, 81.72, 82.79, 83.44, 83.56, 85.32, 104.89, 104.97, 105.05, 125.57, 125.59, 126.48, 126.88, 126.93, 127.25, 127.28, 132.70, 132.74, 134.44, 134.48, 137.61, 137.64, 161.51, 161.58, 161.64, 167.95, 168.07, 168.46, 172.60, 173.13, 173.81, 202.72, 202.86, 204.52; MS (FAB +ve, HR) Calculated for C$_{16}$H$_{16}$FN$_2$O$_5$ (MH+) 335.1043. found 335.1044.

Example 9

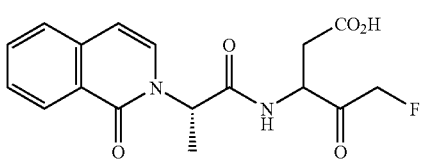

5-Fluoro-4-oxo-3-[(S)-2-(1-oxo-1H-isoquinolin-2-yl)-propionylamino]-pentanoic acid (1C-2) was prepared in a manner similar to that described in Example 1 to provide a white powder: IR (solid) 1783, 1739, 1646 cm$^{-1}$; $^1$H NMR (400 MHz, DMSO) δ 1.5-1.6 (3H, m), 2.5-3.0 (2H, m), 4.3-4.8 (1.7H, m), 5.0-5.7 (2.3H, m), 6.6-6.7 (1H, m), 7.4-7.6 (2H, m), 7.6-7.8 (2H, m), 8.2 (1H, m), 8.2-8.9 (1H, m); $^{13}$C NMR (100 MHz, DMSO) δ 16.07, 16.71, 16.80, 17.03, 17.28, 17.32, 32.99, 34.58, 34.71, 52.24, 52.46, 52.82, 52.88, 53.06, 53.20, 53.49, 53.80, 54.18, 83.43, 83.52, 85.20, 85.29, 105.19, 105.33, 105.37, 105.46, 105.49, 125.43, 125.48, 125.53, 125.57, 126.35, 126.42, 126.87, 126.91, 126.94, 127.02, 127.41, 127.49, 127.58, 130.28, 130.44, 130.50, 130.57, 131.47, 132.81, 137.09, 137.11, 137.15, 161.13, 161.26, 161.34, 161.42, 170.74, 170.91, 171.18, 171.30, 172.04, 172.09, 172.31, 173.15, 173.18, 202.56, 202.68, 202.70, 202.82; MS (FAB +ve, HR) Calculated for C$_{17}$H$_{18}$FN$_2$O$_5$ (MH+) 349.1200. found 349.1198.

Example 10

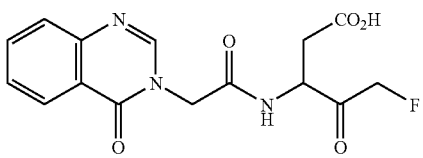

5-Fluoro-4-oxo-3-[2-(1-oxo-1H-isoquinolin-2-yl)-acetylamino]-pentanoic acid (1C-3) was prepared in a manner similar to that described in Example 2 to provide a white powder: IR (solid) 1784, 1721, 1667 cm$^{-1}$; $^1$H NMR (400 MHz, DMSO) δ 2.6-3.0 (1.9H, m), 3.2 (0.1H, m), 4.3-4.6 (0.6H, m), 4.6-4.7 (1H, m) 4.7 (2H, m), 5.1-5.4 (1.4H, m), 7.5-7.6 (1H, m), 7.7 (1H, m), 7.8-7.9 (1H, m), 8.1-8.2 (1H, m), 8.3-8.4 (1H, m), 8.6-9.0 (1H, m); $^{13}$C NMR (100 MHz, DMSO) δ 33.17, 34.85, 48.25, 48.54, 48.62, 47.68, 52.22, 53.01, 80.99, 81.62, 82.75, 83.35, 83.51, 85.28, 121.75, 126.39, 127.38, 127.43, 127.48, 127.52, 134.85, 134.89, 148.13, 148.19, 148.88, 149.01, 160.47, 160.56, 160.61, 167.32, 167.46, 167.80, 172.04, 173.06, 173.70, 202.55, 202.69, 203.59, 204.52; MS (FAB +ve, HR) Calculated for C$_{15}$H$_{15}$FN$_3$O$_5$ (MH+) 336.0996. found 336.0996.

Example 11

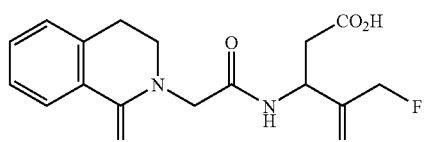

5-Fluoro-4-oxo-3-[2-(1-oxo-3,4-dihydro-1H-isoquinolin-2-yl)-acetylamino]-pentanoic acid (1C-4) was prepared from 3,4-dihydro-1H-isoquinolin-1-one (Norman et al, *J. Med. Chem.*, 1994, 37, 2552) in a manner similar to that described in Example 1 to provide a white powder: IR (solid) 1793, 1655, 1539, 1209, 1175, 1154, 1062, 1037, 942, 748 cm$^{-1}$; $^1$H NMR (400 MHz, DMSO) δ 2.54-2.95 (4H, m), 4.01-4.81 (5H, m), 4.91-5.60 (3H, br m), 7.24-7.41 (2H, m), 7.50-7.52 (1H, m), 7.95 (1H, m), 8.20-8.65 (1H, br m); $^{13}$C NMR (100 MHz, DMSO) δ 27.6, 33.1, 34.8, 47.2, 47.4, 50.1, 50.4, 52.0, 52.7, 81.2, 81.6, 82.9, 83.5, 85.3, 103.9, 104.0, 127.0, 127.7, 127.8, 129.1, 129.2, 132.1, 132.15, 139.3, 139.4, 164.1, 164.2, 164.3, 168.8, 168.9, 169.4, 172.1, 173.2, 173.9, 202.8, 202.9; $^{19}$F (376 MHz, DMSO) δ −229.9 (t), −230.8 (t), −232.2 (t).

Example 12

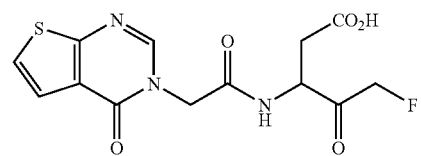

5-Fluoro-4-oxo-3-[2-(4-oxo-4H-thieno[2,3-d]pyrimidin-3-yl)-acetylamino]-pentanoic acid was prepared in a manner similar to that described in Example 2 to provide a white powder: IR (solid) 1666.2, 1723.8, 1783.7 cm$^{-1}$; $^1$H NMR (400 MHz, DMSO) δ 2.6-3.2 (2H, m), 4.3-4.5 (0.3H, m), 4.6-4.8 (1H, m), 4.8 (2H, m), 5.1-5.4 (1.7H, m), 7.4 (1H, m), 7.6 (1H, m), 8.4 (1H, m), 8.7-9.1 (1H, m).

Example 13

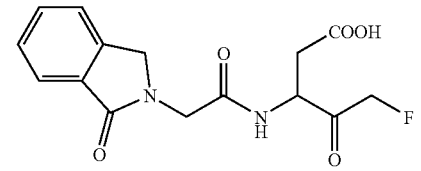

5-Fluoro-4-oxo-3-[2-(1-oxo-1,3-dihydro-isoindol-2-yl)-acetylamino]-pentanoic acid (1F-1) was prepared from 2-(1-oxo-1,3-dihydro-isoindol-2-yl)-acetic acid using methods similar to those described in steps C-E. The title compound was obtained as a white solid. IR (solid) 1782, 1731, 1660, 1532, 1470, 1455, 1419, 1209, 1055, 922 cm$^{-1}$; $^1$H NMR (400 MHz, DMSO-$d_6$) δ 2.58-2.90 (2H, m), 4.20-4.73 5H), 5.18 (1H, dd), 5.29 (1H, dd), 7.50 (1H, m), 7.61 (2H, m), 7.71 (1H, m), 8.38/8.69 (1H, 2d); $^{19}$F NMR (376 MHz, DMSO-$d_6$) δ −227.0 (t), −230.9 (t), −232.6 (t); $^{13}$C NMR (100 MHz, DMSO-$d_6$) δ 34.8, 45.0, 50.9, 52.0, 84.3, 123.2, 123.8, 128.2, 131.9, 132.2, 142.6, 168.2, 168.8, 169.0, 172.1, 202.7.

Example 14

5-Fluoro-4-oxo-3-[(2S)-2-(1-oxo-1,3-dihydro-isoindol-2-yl)-propionylamino]-pentanoic acid (1F-2)

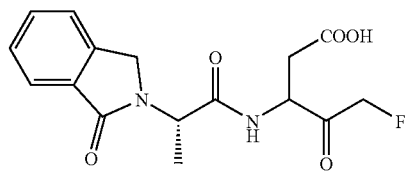

Step F: (2S)-2-(1,3-dioxo-1,3-dihydro-isoindol-2-yl)-propionic acid tert-butyl ester A suspension of (2S) alanine tert-butyl ester hydrochloride (2.05 g, 11.2 mmol), diisopropylethylamine (1.83 mL, 10.6 mmol) and phthalic anhydride (1.48 g, 10 mmol) in toluene (10 mL) was refluxed for 3 hours under Dean-Stark conditions. The reaction was cooled to room temperature, diluted with Et$_2$O, washed with 1N HCl and then with aq. sat. NaHCO$_3$. The organic layer was dried (MgSO$_4$), filtered and evaporated to afford the sub-title compound as a white powder (2.465 g, 90%): $^1$H NMR (400 MHz CDCl$_3$) δ 1.45 (9H, s), 1.68 (3H, d), 4.90 (1H, q), 7.75 (2H, d), 7.88 (2H, d).

Step G: (2S)-2-(1-hydroxy-3-oxo-1,3-dihydro-isoindol-2-yl)-propionic acid tert-butyl ester To a solution of (2S)-2-(1,3-dioxo-1,3-dihydro-isoindol-2-yl)-propionic acid tert-butyl ester (426 mg, 1.55 mmol) in a mixture of THF (10 mL) and MeOH (2 mL) was added sodium borohydride (181 mg, 4.8 mmol) in one portion. The reaction mixture was stirred for 30 minutes before solvents were evaporated at room temperature and the residue was columned on silica (Petrol/AcOEt, 8/2) to afford the sub-title compound as colorless oil (284 mg, 66%): $^1$H NMR (400 MHz CDCl$_3$) δ 1.38-1.40 (9H, 2s), 1.57-1.60 (3H, 2d), 4.38-4.45 (1H, m), 4.65-4.76 (1H, m), 5.81-6.01 (1H, 2d), 7.33-7.64 (4H, d).

Step H: (2S)-2-(1-oxo-1,3-dihydro-isoindol-2-yl)-propionic acid

To a solution of (2S)-2-(1-hydroxy-3-oxo-1,3-dihydro-isoindol-2-yl)-propionic acid tert-butyl ester (271 mg, 0.98 mmol) in TFA (5 mL) was added triethylsilane (170 mg, 1.47 mmol) in one portion. The reaction mixture was stirred for 1 hour before the solvents were evaporated. The residue was triturated with Et$_2$O and filtered to deliver the sub-title compound as a white solid (165 mg, 82%): $^1$H NMR (400 MHz DMSO-$d_6$) δ 1.51 (3H, d), 4.49-4.55 (2H, m), 4.85 (1H, q), 7.51-7.71 (4H, m), 12.90 (1H, br s).

5-Fluoro-4-oxo-3-[(2S)-2-(1-oxo-1,3-dihydro-isoindol-2-yl)-propionylamino]-pentanoic acid was prepared from (2S)-2-(1-oxo-1,3-dihydro-isoindol-2-yl)-propionic acid using methods similar to those described in steps C-E above. The title compound was obtained as a white solid. IR (solid) 1736, 1660, 1527, 1450, 1360, 1226, 1222 cm$^{-1}$; $^1$H NMR (400 MHz, DMSO-$d_6$) δ 1.42-1.46 (3H, m), 2.68 (1H, m), 2.74 (1H, m), 4.52-4.63 (3H, m), 4.85 (1H, m), 5.14-5.76 (2H, br m,), 7.48-7.53 (1H, m), 7.62-7.63 (2H, m), 7.70-7.72 (1H, m), 8.66 (1H, br s), 12.50 (1H, br s); $^{19}$F NMR (376 MHz, DMSO-$d_6$) δ −232.6; $^{13}$C NMR (100 MHz, DMSO-$d_6$) δ 16.0, 34.4, 47.4, 49.9, 52.2, 123.1/123.2, 123.8, 128.2, 131.8, 132.4, 142.8, 167.9, 172.5.

Example 15

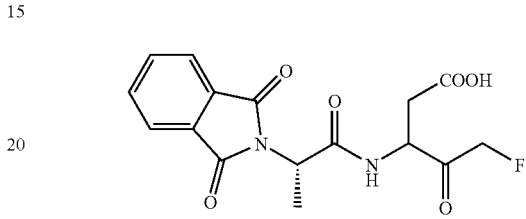

5-Fluoro-4-oxo-3-[(2S)-2-(1,3-dioxo-1,3-dihydro-isoindol-2-yl)-propionylamino]-pentanoic acid (1F-3) was prepared from (2S)-2-(1,3-dioxo-1,3-dihydro-isoindol-2-yl)-propionic acid tert-butyl ester using methods similar to those described above in steps F and then C-E. The title compound was obtained as a colorless viscous oil.

IR (film) 1777, 1706, 1644, 1532, 1383, 1363, 1204, 1158, 1045 cm$^{-1}$; $^1$H NMR (400 MHz, DMSO-$d_6$) δ 1.49-1.56 (3H, m), 2.42-2.49 (1H, m), 2.74-2.82 (1H, m), 4.31-4.90 (2H, m), 4.91-5.39 (2H, m), 7.86-7.92 (4H, m), 8.59/8.72 (1H, 2d); $^{19}$F NMR (376 MHz, DMSO-$d_6$) δ −226.7, −226.8, −231.0, −232.2, −233.0, −233.1; $^{13}$C NMR (100 MHz, DMSO-$d_6$) δ 15.1/15.2, 34.3/34.4, 48.0/48.1, 52.2/52.5, 84.1/84.2, 123.4/123.5, 123.5/123.7, 132.2, 134.7/134.8, 134.8/135.1, 167.7, 169.7/169.8, 172.0/172.1, 202.3.

Example 16

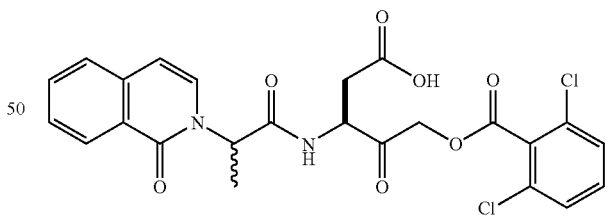

2,6-Dichloro-benzoic acid 4-carboxy-2-oxo-3-[2-(1-oxo-1H-isoquinolin-2-yl)-propionylamino]-butyl ester (1C-5)
Step I: 2,6-Dichloro-benzoic acid 4-tert-butoxycarbonyl-2-hydroxy-3-[2-(1-oxo-1H-isoquinolin-2-yl)-propionylamino]-butyl ester A stirred solution of 2-(1-oxo-1H-isoquinolin-2-yl)-propionic acid (150 mg, 0.7 mmol) and 2,6-dichloro-benzoic acid 3-allyloxycarbonylamino-4-tert-butoxycarbonyl-2-hydroxy-butyl ester (319 mg, 0.7 mmol) in a mixture of anhydrous DMF (1.5 ml) and CH$_2$Cl$_2$ (4.5 ml) at room temperature was treated with a catalytic amount of bis(triphenylphosphine) palladium (II) chloride, followed by dropwise addition of tributyltin hydride (279 μm, 11.0 mmol). After 5 mins, HOBt (186 mg, 1.4 mmol) was added, the reaction mixture was cooled to 0° C., EDC (132 mg, 0.7 mmol) was added and the reaction mixture was allowed to stir for 16 h warming slowly to room temperature. The reaction mixture was poured onto ice-cold 1M HCl and extracted with EtOAc and then the organic phase was washed with saturated aqueous sodium bicarbonate, followed by saturated sodium chloride solution, dried ($Na_2SO_4$), filtered and concentrated. The residue was triturated with petrol and then purified by flash using as eluent 1:1 petrol/EtOAc to afford the sub-title compound as a colorless foam (190 mg, 48%); $^1$H NMR (400 MHz $CDCl_3$) δ 1.3-1.5 (10H, m), 1.65-1.75 (3H, 2×d), 2.5-2.7 (2H, m), 4.1-4.5 (3H, m), 5.6 (1H, 2×q), 6.6 (1H, 2×d), 7.1-7.6 (8H, m), 7.7 (1H, m), 8.4 (1H, d).

Step J: 2,6-Dichloro-benzoic acid 4-tert-butoxycarbonyl-2-oxo-3-[2-(1-oxo-1H-isoquinolin-2-yl)-propionylamino]-butyl ester A stirred solution of 2,6-dichloro-benzoic acid 4-tert-butoxycarbonyl-2-hydroxy-3-[2-(1-oxo-1H-isoquinolin-2-yl)-propionylamino]-butyl ester (183 mg, 0.32 mmol) in anhydrous DCM (3 ml) was treated with 1,1,1-triacetoxy-1,1-dihydro-1,2-benziodoxol-3(1H)-one (147 mg, 0.34 mmol) at 0° C. The resulting mixture was kept at 0° C. for 5 h, diluted with DCM, then poured into a 1:1 mixture of saturated aqueous sodium hydrogen carbonate and saturated aqueous sodium thiosulphate. The organic layer was removed and the aqueous layer re-extracted with DCM. The combined organic extracts were dried ($Na_2SO_4$), filtered and concentrated. The residue was purified by flash chromatography using as eluent 60:40 petrol/EtOAc to afford the sub-title compound as a colorless foam (116 mg, 64%): $^1$H NMR (400 MHz, $CDCl_3$) δ 1.2-1.4 (9H, 2×s), 1.7 (3H, d), 2.7-3.0 (2H, m), 4.9-5.1 (4H, m), 5.8 (1H, m), 6.6 (1H, 2×d), 7.2-7.6 (7H, m), 8.4 (1H, m); MS (FAB +ve) 576.

Step K: 2,6-Dichloro-benzoic acid 4-carboxy-2-oxo-3-[2-(1-oxo-1H-isoquinolin-2-yl)-propionylamino]-butyl ester Trifluoroacetic acid (2 ml) was added to a stirred ice cold solution of 2,6-dichloro-benzoic acid 4-tert-butoxycarbonyl-2-oxo-3-[2-(1-oxo-1H-isoquinolin-2-yl)-propionylamino]-butyl ester (110 mg, 0.19 mmol) in anhydrous dichloromethane (2 ml). The mixture was stirred at 0° C. for 1 h and at room temperature for 0.5 h. The reaction mixture was concentrated under reduced pressure and then the residue was redissolved in dry dichloromethane. This process was repeated several times in order to remove excess trifluoroacetic acid. The residue was then lyophilized twice from HPLC grade water and then purified by reverse phase HPLC using a gradient eluent of 10:90 $CH_3CN$:water to 100:0 $CH_3CN$:water to afford the title compound as white solid (17 mg, 16%): IR (solid) 3295, 1736, 1648, 1618, 1590 $cm^{-1}$; $^1$H NMR (400 MHz, DMSO) 1.57 (3H, 2×d), 2.64-2.80 (2H, m), 4.73 (1H, m), 5.14-5.33 (2H, m), 5.44-5.53 (1H, m), 6.67 (1H, m), 7.44-7.74 (7H, m), 8.20 (1H, d), 8.77-8.83 (1H, bd); $^{13}$C NMR (100 MHz, DMSO) 16.72, 16.90, 53.77, 105.36, 105.49, 125.48, 126.37, 126.90, 127.49, 128.85, 130.52, 130.67, 131.15, 132.47, 132.82, 132.93, 137.09, 137.12, 161.38, 163.56, 163.64, 171.15, 171.25; MS (FAB +ve, HR) Calculated for $C_{24}H_{20}Cl_2N_2O_7$ (MH+) 519.0726. found 519.0701.

Example 17

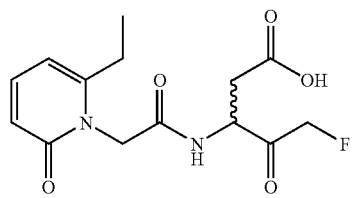

5-Fluoro-3-[2-(6-ethyl-2-oxo-2H-pyridin-1-yl)-acetylamino]-4-oxo-pentanoic acid (1A-6) was prepared in a manner similar to that described in Example 2 to provide colorless crystals: IR (solid) 1792.9, 1664.9, 1644.4, 1547.1, 1209.1, 1045.2, 1019.6, 922.3 $cm^{-1}$; $^1$H NMR (400 MHz, DMSO) δ 1.15 (3H, t), 2.52-2.71 (3H, m), 2.74-2.93 (1H, m), 4.28-4.81 (4H, m), 5.25 (1H, m), 6.10 (1H, m), 6.29 (1H, m), 7.37 (1H, m), 7.85-8.85 (1H, m), 12.50 (1H, brs); $^{13}$C NMR (100 MHz, DMSO) δ 12.4, 12.45, 25.5, 25.6, 25.7, 33.2, 34.8, 45.6, 46.1, 47.7, 52.2, 52.8, 81.2, 83.0, 83.4, 83.6, 85., 103.7, 103.8, 103.9, 104.0, 116.4, 116.5, 139.9, 140.0, 152.6, 162.7, 162.9, 167.8, 167.9, 168.3, 172.1, 173.1, 202.7, 202.9; $^{19}$F (376 MHz, DMSO)-226.9 (t), -231.6 (t), -233.1 (t); MS (FAB +ve, HR) Calculated for $C_{14}H_{17}FN_2O_5$ (M+) 312.1122. found 312.1115.

Example 18

5-Fluoro-4-oxo-3-[(2S)-2-(4-oxo-4H-quinazolin-3-yl)-propionylamino]-pentanoic acid

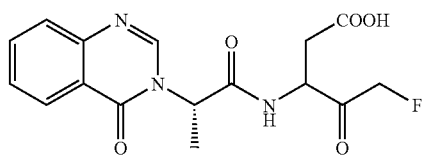

Step L: (2S)-2-formylamino-propionic acid tert-butyl ester

To a suspension of (2S) alanine tert-butyl ester hydrochloride (3.63 g, 20 mmol) in a mixture of ethyl formate (10 mL) and DCM (5 mL) was added diisopropylethylamine (3.83 mL, 22 mmol) and the reaction mixture was refluxed overnight. The solvents were evaporated and the residue was then triturated in $Et_2O$ and filtrated. The filtrates were evaporated and the residue was filtered through a short pad of silica using ethyl acetate as eluent. Evaporation of the solvent afforded the sub-title compound as a colorless oil which crystallised upon standing (2.806 g, 81%): $^1$H NMR (400 MHz $CDCl_3$) δ 1.43 (3H, d), 1.50 (9H, s), 4.55 (1H, m), 6.31 (1H, br s), 8.16 (1H, s).

Step M: (2S)-2-(N-(2-Azido-benzoyl)-N-formylamino)-propionic acid tert-butyl ester A stirred solution of (2S)-2-formylamino-propionic acid tert-butyl ester (3.524 g, 20.3 mmol) in anhydrous THF (50 mL) was treated at −78° C. with LDA (20.3 mmol) and the reaction was stirred for 15 min. A solution of 2-azidobenzoyl chloride (T. Okawa, T. Sugimori, S. Eguchi and A. Kakehi, Heterocycles, 1998, 47, 1, 375-382) (20.6 mmol) in anhydrous THF (20 mL) was then added dropwise and the reaction mixture was stirred at −78° C. for 1 h before being quenched with saturated aq. NH$_4$Cl. The reaction was allowed to warm to room temperature and the organic layer was washed with saturated aq. NH$_4$Cl, dried (MgSO$_4$), filtered and evaporated and residue was purified by flash chromatography (20% ethyl acetate in hexane) to afford the sub-title compound as a pale yellow oil (3.437 g, 53%): $^1$H NMR (400 MHz CDCl$_3$) δ 1.49 (9H, s), 1.60 (3H, d), 5.18 (1H, m), 7.27 (2H, m), 7.40 (1H, d), 7.59 (1H, t), 8.60 (1H, s).

Step N: (2S)-2-(4-oxo-4H-quinazolin-3-yl)-propionic acid tert-butyl ester

Triphenylphosphine (3.41 g, 13.0 mmol) was added portionwise to a solution of (2S)-2-(N-(2-azido-benzoyl)-N-formylamino)-propionic acid tert-butyl ester (3.437 g, 10.80 mmol) in xylene (70 mL) at room temperature. The reaction mixture was stirred at room temperature until the evolution of nitrogen ceased (approx. 1 h), and then refluxed for 20 h. The volatiles were evaporated and the residue was purified by flash chromatography (30% ethyl acetate in hexane) to afford the sub-title compound as a colorless oil (2.221 g, 75%). $^1$H NMR (400 MHz C$_6$D$_6$) δ 1.30 (3H, d), 1.34 (9H, s), 4.97 (1H, q), 7.08 (1H, m), 7.31 (1H, m), 7.81 (1H, s), 7.86 (1H, d), 8.55 (1H, m).

Step O: (2S)-2-(4-oxo-4H-quinazolin-3-yl)-propionic acid

A solution of (2S)-2-(4-oxo-4H-quinazolin-3-yl)-propionic acid tert-butyl ester (1.434 g, 5.23 mmol) in TFA (25 mL) was stirred at room temperature for 5 h. The mixture was concentrated under reduced pressure and the residue was dissolved in dry DCM. This process was repeated several times to remove excess TFA. The gum was triturated with diethyl ether, filtrated and washed several times with diethyl ether to afford the sub-title compound as a white powder (1.626 g, 94%): $^1$H NMR (400 MHz DMSO-d$_6$) δ 1.67 (3H, d), 5.26 (1H, q), 7.58 (1H, m), 7.71 (1H, d), 7.87 (1H, m), 8.15 (1H, m), 8.44 (1H, s).

5-Fluoro-4-oxo-3-[(2S)-2-(4-oxo-4H-quinazolin-3-yl)-propionylamino]-pentanoic acid was prepared from (2S)-2-(4-oxo-4H-quinazolin-3-yl)-propionic acid using methods similar to those described above in steps C-E. The title compound was obtained as a white solid. IR (solid) 1717, 1663 cm$^{-1}$; $^1$H NMR (400 MHz, DMSO-d$_6$) δ 1.63-1.67 (3H, 2t), 2.51-2.91 (2H, m), 4.30-4.71 (1.5H, m,), 5.09-5.51 (2.5H, m), 7.55-7.58 (1H, m), 7.71 (1H, d), 7.84-7.88 (1H, m), 8.14-8.16 (1H, m), 8.39-8.41 (1H, m), 8.59, 8.62, 8.79, 8.84, 8.90 (1H, m); $^{19}$F NMR (376 MHz, DMSO-d$_6$) δ −75.41 (s), −226.74 (t), −226.82 (t), −230.63 (t), −231.40 (t), −232.85 (t), −232.95 (t); $^{13}$C NMR (100 MHz, DMSO-d$_6$) δ 16.65, 16.72, 16.86, 17.28, 34.56, 34.62, 47.74, 52.27, 52.34, 52.49, 53.14, 53.52, 83.41, 85.18, 121.59, 121.65, 126.52, 126.65, 127.30, 127.34, 127.49, 134.93, 146.73, 146.79, 147.70, 147.73, 158.45, 158.83, 160.40, 170.34, 170.52, 170.63, 172.01, 172.07, 172.12, 202.47, 202.51, 202.61.

Example 19

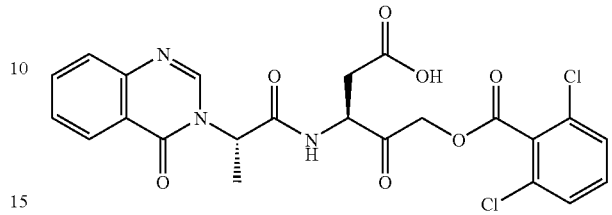

2,6-Dichloro-benzoic acid 4-carboxy-2-oxo-3-[2-(4-oxo-4H-quinazolin-3-yl)-propionylamino]-butyl ester (1C-7) was prepared from (2S)-2-(4-oxo-4H-quinazolin-3-yl)-propionic acid using the procedures described above in Steps I to K to afford the title compound as a white solid (17 mg, 57%) IR (solid) 1735, 1676, 1612 cm$^{-1}$; $^1$H NMR (400 MHz, DMSO) δ 1.61-1.68 (3H, m), 2.59-2.89 (2H, m), 4.72 (1H, m), 5.19-5.31 (2H, dd), 5.45 (1H, m), 7.54-7.68 (4H, m), 7.71 (1H, d), 7.86 (1H, m), 8.11 (1H, m), 8.34 (1H, m), 8.60, 8.80, 8.96 (1H, 3×d); $^{13}$C NMR (100 MHz, DMSO) δ 16.75, 17.25, 32.91, 34.76, 47.74, 52.21, 53.22, 65.64, 68.21, 121.65, 127.41, 128.80, 128.87, 131.04, 132.42, 132.97, 134.89, 146.66, 147.88, 160.41, 163.63, 170.65, 172.02, 200.10; $^{19}$F (376 MHz, DMSO)-74.71 (s); MS (FAB +ve, HR) Calculated for C$_{23}$H$_{19}$Cl$_2$N$_3$O$_7$ (MH+-TFA) 520.0678. found 520.0677.

Example 20

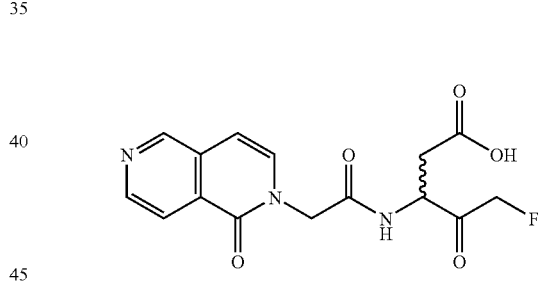

5-fluoro-4-oxo-3-[2-(1-oxo-1H-[2,6]naphthyridin-2-yl)-acetylamino]-pentanoic acid (1E-2)

Step P: (1-oxo-1H-[2,6]naphyridin-2-yl)-acetic acid tert-butyl ester

To a stirred solution of 2,6-naphthyridin-1-(2H)-one (80.7 mg, 0.55 mmol) in dry THF (0.5 mL) was added NaH (27 mg, 0.66 mmol, 60% in oil) in one portion. The resulting suspension was stirred at room temperature for 15 minutes and a further aliquot of dry THF (0.5 mL) was added. After a further 5 minutes tert-butyl bromoacetate (129 mg, 0.66 mmol) was added in one portion. After four hours the solvent was removed under reduced pressure and the resultant gum was partitioned between water and EtOAc. The layers were separated and the aqueous layer was further extracted with EtOAc (3×15 mL). The organics were combined, dried (Na$_2$SO$_4$), filtered and concentrated under reduced pressure. Column chromatography (2% MeOH in EtOAc) gave sub-title compound as a deep orange solid (120 mg, 84%).

¹H NMR (CDCl₃): 1.5 (9H, s, ᵗBu), 4.65 (2H, s, —CH₂—), 6.6 (1H, d, Ar), 7.1 (1H, d, Ar), 8.2 (1H, d, Ar), 8.7 (1H, d, Ar), 9.0 (1H, s, Ar)

Step Q: (1-oxo-1H-[2,6]naphyridin-2-yl)-acetic acid

To a stirred solution of (1-oxo-1H-[2,6]naphyridin-2-yl)-acetic acid tert-butyl ester in dry DCM (2.5 mL) cooled in an ice-bath was added TFA (2.5 mL) in one portion. The resultant light yellow solution was stirred at 0° C. for 30 minutes and at room temperature for 30 minutes. Removal of solvent and TFA under reduced pressure and repeated azeotroping of the resulting material with aliquots of dry DCM (10 mL×5) gave an orange-brown gum (143 mg, quant.) that was used without further purification.

5-fluoro-4-oxo-3-[2-(1-oxo-1H-[2,6]naphthyridin-2-yl)-acetylamino]-pentanoic acid was prepared from (1-oxo-1H-[2,6]naphyridin-2-yl)-acetic acid using methods similar to those described in steps C-E. The title compound was obtained as a bright yellow solid (46 mg, 74%): IR (Solid) 1628.0, 1664.5, 1785.3 cm⁻¹; ¹H NMR (DMSO) δ 2.6-3.2 (2H, m), 4.3-4.5 (0.5H, m), 4.6 (1H, m), 4.7-4.8 (2H, m), 5.1-5.4 (1.5H, m), 6.8 (1H, m), 7.6 (1H, m), 8.1 (1H, m), 8.6 (0.3H, m), 8.6-8.7 (1H, m), 8.7-9.0 (0.7H, m), 9.1-9.2 (1H, s); ¹⁹F (DMSO) δ −226.5 (minor), −226.8, −230.9 (minor), −231.4, −233.0; ¹³C (DMSO) δ 33.16, 34.83, 47.60, 51.32, 51.64, 52.19, 52.93, 80.97, 81.65, 82.73, 83.38, 83.53, 85.30, 102.37, 102.49, 102.56, 120.13, 120.19, 130.42, 130.45, 132.26, 136.84, 136.93, 145.14, 145.23, 149.34, 149.39, 160.34, 160.42, 160.48, 167.44, 167.56, 167.95, 172.09, 173.12, 173.77, 202.64, 202.78; HRMS Calc: 336.099574. Found: 336.098907, +2.0 ppm Example 21

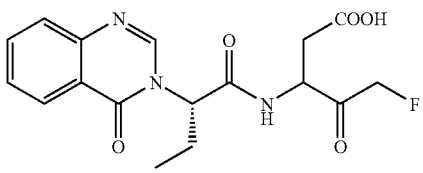

5-Fluoro-4-oxo-3-[(2S)-2-(4-oxo-4H-quinazolin-3-yl)-butyrylamino]-pentanoic acid (1C-8) was prepared from 2-azidobenzoyl chloride (T. Okawa, T. Sugimori, S. Eguchi and A. Kakehi, Heterocycles, 1998, 47, 1, 375-382) and 2-aminobutyric acid tert-butyl ester hydrochloride, using methods similar to those described above in steps L-O then C-E. The title compound was obtained as a white powder. IR (solid) 1722, 1665, 1365, 1203, 1136, 1055 cm⁻¹; ¹H NMR (400 MHz, DMSO-d₆) δ 1.81-1.89 (3H, m), 2.03-2.27 (2H, m), 2.55-2.91 (2H, m), 4.28-4.74 and 5.11-5.42 (4H, 2m), 7.54 (1H, m), 7.70 (1H, m), 7.87 (1H, m), 8.14 (1H, m), 8.39 (1H, m), 8.89-9.01 (1H, m); ¹⁹F NMR (376 MHz, DMSO-d₆) δ −75.4 (s, TFA salt), −226.7 (t), −226.8 (t), −230.4 (t), −231.0 (t), −232.6 (t), −232.7 (t); ¹³C NMR (100 MHz, DMSO-d₆) δ 9.16, 22.2/22.4, 33.1, 50.7/50.9, 56.5/56.9, 82.8/82.9, 119.9/ 120.0, 125.2, 125.9, 126.1, 133.6, 145.3/145.4, 146.0/146.0, 159.2, 168.5/168.6 170.5/170.5, 201.1/201.1.

Example 22

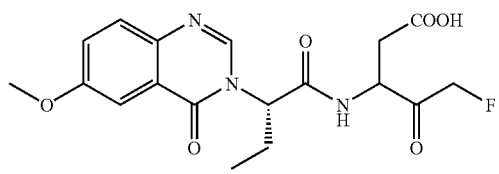

5-Fluoro-4-oxo-3-[(2S)-2-(6-methoxy-4-oxo-4H-quinazolin-3-yl)-butyrylamino]-pentanoic acid (1C-9) was prepared from 2-azido-5-methoxybenzoyl chloride (T. Okawa, T. Sugimori, S. Eguchi and A. Kakehi, Heterocycles, 1998, 47, 1, 375-382) and 2-aminobutyric acid tert-butyl ester hydrochloride, using methods similar to those described in steps L-O then C-E. The title compound was obtained as a white powder. IR (solid) 1732, 1660, 1493, 1355, 1222, 1198, 1026, 831 cm⁻¹; ¹H NMR (400 MHz, DMSO-d₆) δ 080-0.84 (3H, m), 1.99-2.22 (2H, m), 2.56 (2H, br s), 3.17 (1H, br s), 3.88 (3H, s), 4.50-4.58 (1H, m), 4.99-5.31 (2H, br), 5.37-5.45 (1H, m), 7.45-7.47 (1H, m), 7.51-7.53, 1H, m), 7.64-7.66 (1H, m), 8.27-8.29 (1H, m), 8.88-8.95 (1H, m); ¹⁹F NMR (376 MHz, DMSO-d₆) δ −75.1 (s, TFA salt), −231.2 (br); ¹³C NMR (100 MHz, DMSO-d₆) δ 10.6/10.7, 24.0/24.2, 56.0, 57.6/57.8, 106.6, 127.2/127.3, 124.4, 129.2, 142.2, 144.6, 158.3, 160.5, 169.9.

Example 23

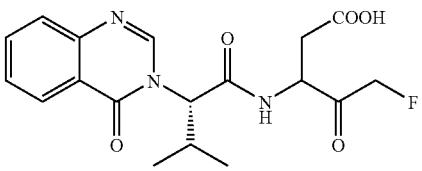

5-Fluoro-4-oxo-3-[(2S)-3-methyl-2-(4-oxo-4H-quinazolin-3-yl)-butyrylamino]-pentanoic acid (1C-10) was prepared from 2-azidobenzoyl chloride and valine tert-butyl ester hydrochloride, using methods similar to those described above in steps L-0 and then steps C-E. After step D, the two diastereoisomers were separated by three successive crystallisation in Et₂O/Petrol (1/1). These two diastereoisomers were used independently in step E and were each obtained as white powders.
Diastereoisomer 1:
IR (solid) 1732, 1660, 1365, 1231, 1212, 1198 cm⁻¹; ¹H NMR (400 MHz, DMSO-d₆) δ 0.75-1.13 (6H, m), 1.24-1.53 (1H, m), 2.57-2.92 (2H, m), 4.13-5.39 (4H, m), 7.56-7.59 (1H, m), 7.70-7.72 (1H, m), 7.85-7.88 (1H, m), 8.17-8.19 (1H, m), 8.52-8.57 (1H, m), 8.92-9.25 (1H, m); ¹⁹F NMR (376 MHz, DMSO-d₆) δ −75.3 (s, TFA), −226.8 (t), −232.3 (t); ¹³C NMR (400 MHz, DMSO-d₆) δ 19.6, 20.2, 30.4, 35.2, 52.4, 61.4, 84.7, 121.8, 127.4, 128.0, 128.1, 135.6, 147.7, 147.9, 161.1, 169.8, 172.3, 203.0.
Diastereoisomer 2
IR (solid) 1732, 1660, 1607, 1360, 1226, 1212, 1193 cm⁻¹; ¹H NMR (400 MHz, DMSO-d₆) δ 0.75-1.11 (6H, m), 1.24-1.35 (1H, m), 2.55-2.87 (2H, m), 4.37-5.35 (4H, m), 7.55-

7.57 (1H, m), 7.67-7.71 (1H, m), 7.84-7.88 (1H, m), 8.16-8.18 (1H, m), 8.55-8.58 (1H, m), 8.98-9.25 (1H, m); $^{19}$F NMR (376 MHz, DMSO-d$_6$) δ −75.3 (s, TFA), −226.3 (t), −231.8 (t); $^{13}$C NMR (100 MHz, DMSO-d$_6$) δ 19.1, 19.6, 30.2, 34.5, 52.0, 60.4, 84.5, 121.2, 126.9, 127.5, 127.6, 135.1, 146.1, 147.3, 160.5, 169.4, 171.8, 202.5.

Example 24

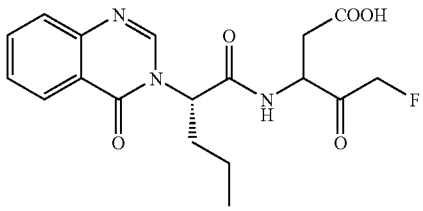

5-Fluoro-4-oxo-3-[(2S)-2-(4-oxo-4H-quinazolin-3-yl)-pentanoylamino]-pentanoic acid (1C-11) was prepared from 2-azidobenzoyl chloride and (2S) 2-amino-pentanoic acid tert-butyl ester hydrochloride, using methods similar to those described above in steps L-O then in steps C-E. The title compound was obtained as a white solid. IR (solid) IR (solid) 2918, 1736, 1665, 1607, 1365, 1226, 1222, 1193 cm$^{-1}$; $^1$H NMR (400 MHz, DMSO-d$_6$) δ 0.87-0.88 (3H, m), 1.21-1.23 (2H, m), 2.08-2.09 (2H, m), 2.44-2.90 (2H, m), 4.29-5.58 (4H, m), 7.55-7.59 (1H, m), 7.70-7.72 (1H, m), 7.84-7.88 (1H, m), 8.15-8.17 (1H, m), 8.41 (1H, s), 8.72, 9.01 (1H, m); $^{19}$F NMR (376 MHz, DMSO-d$_6$) δ −75.3 (s, TFA salt), −226.7 (t), −226.8 (t), −230.4 (t), −231.0 (t), −232.6 (t), −232.7 (t); $^{13}$C NMR (100 MHz, DMSO-d$_6$) δ 13.6/13.6, 19.0, 32.2/32.3, 34.6/34.6, 52.2/52.4, 55.9/56.4, 84.3/84.5, 121.4/121.5, 126.7, 127.4, 127.5, 135.0, 146.8/146.9, 147.6/147.6, 160.6, 170.1/170.6, 172.0/172.0, 202.5/202.6.

Example 25

5-Fluoro-4-oxo-3-[(2S)-2-(6-oxo-6H-pyrimidin-1-yl)-butyrylamino]-pentanoic acid (1G-1)

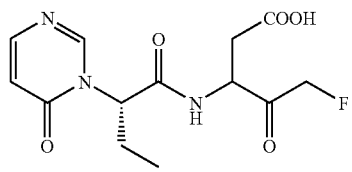

Step R: 3-Exo-tert-butoxycarbonylaminobicyclo[2.2.1]-hept-5-ene-2-exo-carboxylic acid To a solution of 3-exo-aminobicyclo[2.2.1]-hept-5-ene-2-exo-carboxylic acid (1.048 g, 6.84 mmol) in MeCN (10 mL) was added at 0° C. disopropylethylamine (1.311 mL, 7.53 mmol), followed by di-tert-butylcarbonate (1.941 g, 8.89 mmol). The reaction was allowed to warm to room temperature and stirred for 4 hours. The reaction mixture was partitioned between ethyl acetate and water and the aqueous layer was acidified with 2N HCl before being extracted with ethyl acetate. The organic phase was washed with brine, dried (MgSO$_4$), filtered and evaporated to give the sub-title compound as a white powder (1.635 g, 94%): $^1$H NMR (400 MHz CDCl$_3$) δ 1.45 (9H, s), 1.67 (1H, m), 2.18 (1H, m), 2.60 (1H, m), 2.74 (1H, s), 2.99 (1H, s), 3.96 (1H, m), 6.19 (2H, m), 6.98 (1H, m), 12.37 (1H, br s).

Step S: (2S)-2-[(3-Exo-tert-butoxycarbonylamino-bicyclo[2.2.1]-hept-5-ene-2-exo-carbonyl)-amino]butyric acid tert-butyl ester A stirred mixture of 3-exo-tert-butoxycarbonylamino bicyclo[2.2.1]-hept-5-ene-2-exo-carboxylic acid (728 mg, 2.87 mmol), (2S)-2-aminobutyric acid tert-butyl ester hydrochloride (619 mg, 3.16 mmol), diisopropylethylamine (409 mg, 3.16 mmol), HOBt (415 mg, 3.16 mmol) and DMAP (386 mg, 3.16 mmol) and anhydrous THF (20 ml) was cooled to 0° C. then EDC (606 mg, 3.16 mmol) was added. The mixture was allowed to warm to room temperature during 16 h then concentrated under reduced pressure. The residue was purified by flash chromatography (20% ethyl acetate in hexane) to afford the sub-title compound as a white solid (1.116 g, 98%): $^1$H NMR (400 MHz CDCl$_3$) δ 0.89-0.94 (3H, m), 1.42-1.54 (10H, m), 1.64-1.96 (2H, m), 2.13-2.15 (1H, m), 2.35-2.39 (1H, m), 2.70-2.74 (1H, m), 2.88-2.93 (1H, m), 3.84-3.95 (1H, m), 4.37-4.47 (1H, m), 5.44-5.84 (1H, 2d), 6.14-6.23 (3H, m).

Step T: (2S)-2-[(3-Exo-amino-bicyclo[2.2.1]-hept-5-ene-2-exo-carbonyl)-amino]butyric acid tert-butyl ester To a solution of (2S)-2-[(3-Exo-tert-butoxycarbonylamino-bicyclo[2.2.1]-hept-5-ene-2-exo-carbonyl)-amino]butyric acid tert-butyl ester (1.046 g, 2.65 mmol) in ethyl acetate (2.5 mL) was added 2M HCl in ethyl acetate (10 mL). The reaction was stirred at room temperature for 4 h, then washed with water, saturated aq. NaHCO$_3$ and brine. The combined aqueous layers were extracted with DCM. The combined organic phases were dried (MgSO$_4$), filtered and evaporated to afford the sub-title compound as a colorless oil (677 mg, 87%): $^1$H NMR (400 MHz CDCl$_3$) δ 0.94 (3H, t, J 7.5), 1.48-1.49 (9H, m), 1.55 (1H, m), 1.64-1.94 (4H, m), 2.14-2.20 (1H, m), 2.28-2.30 (1H, m), 2.59-2.61 (1H, m), 2.94-2.98 (1H, m), 3.17-3.21 (1H, m), 4.46-4.52 (1H, m), 6.19 (2H, m), 6.43-6.54 (1H, 2d).

Step U: (2S)-2-(6-oxo-6H-pyrimidin-1-yl)-butyric acid tert-butyl ester

To a solution of (2S)-2-[(3-Exo-amino-bicyclo[2.2.1]-hept-5-ene-2-exo-carbonyl)-amino]butyric acid tert-butyl ester (655 mg, 2.22 mmol) in xylene (10 mL) was added triethylorthoformate (989 mg, 6.67 mmol) and the reaction mixture was refluxed overnight. The solvent was evaporated and the residue purified by flash chromatography (hexane/ethyl acetate 50/50) to afford the sub-title compound as a colorless viscous oil (380 mg, 72%). $^1$H NMR (400 MHz CDCl$_3$) δ 0.98 (3H, t), 1.47 (9H, m), 1.98 (1H, m), 2.28 (1H, m), 5.25 (1H, dd), 6.47 (1H, d), 7.90 (1H, d), 8.14 (1H, s).

5-Fluoro-4-oxo-3-[(2S)-2-(6-oxo-6H-pyrimidin-1-yl)-butyrylamino]-pentanoic acid was prepared from the above compound using procedures similar to those described above in step 0 and then steps C-E.

IR (solid) 1717, 1665, 1527, 1365, 1241, 1155, 841.1775, 1727, 1665, 1551, 1417, 1188, 1136, 1055 cm$^{-1}$; $^1$H NMR (400 MHz, DMSO-d$_6$) δ 0.77-0.81 (3H, m), 1.96-2.14 (2H, m), 2.57-2.86 (2H, m), 4.28-4.66 (1.5H, m), 5.06-5.40 (2.5H, m), 6.41-6.45 (1H, m), 7.93-7.95 (1H, m), 8.47-8.50 (1H, m), 8.71-9.02 (1H, m); $^{19}$F NMR (376 MHz, DMSO-d$_6$) δ −75.4 (s, TFA salt), −226.7 (t), −226.8 (t), −230.4 (t), −231.2 (t), −232.7 (t), −232.8 (t); $^{13}$C NMR (100 MHz, DMSO-d$_6$) δ 10.5/10.6, 23.7/23.9, 34.6/34.7, 52.3/52.5, 57.6/58.1, 84.3// 84.4, 114.7/114.8, 151.9/153.2, 153.3/153.4, 160.5/160.5, 169.6/169.7, 171.9/172.0, 202.5/202.6.

Example 26

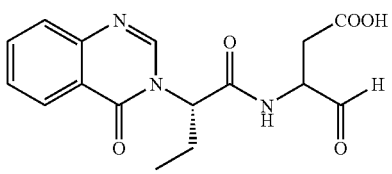

(3S)-4-Oxo-3-[(2S)-2-(4-oxo-4H-quinazolin-3-yl)-butyrylamino]-butanoic acid (1C-12) was prepared from (2S)-2-(4-oxo-4H-quinazolin-3-yl)-butanoic acid (111.1 mg, 0.49 mmol) [prepared from 2-azidobenzoyl chloride and 2-aminobutyric acid tert-butyl ester hydrochloride, using methods similar to those described in steps L-o] and (2RS,3S)-allyloxycarbonylamino-2-benzyloxy-5-oxotetrahydrofuran (153.3 mg, 0.53 mmol) according to the methods described in Vertex Patent WO97/22619. The title compound was obtained as a off-white solid (45.5 mg, 29% over final two steps): $^1$H NMR (400 MHz, CD$_3$OD) δ 0.95-1.15 (3H, m), 2.00-2.38 (2H, m), 2.45-2.90 (2H, m), 4.25-4.45 (1H, m), 4.50-4.80 (1H, m), 5.40-5.75 (1H, m), 7.75-7.90 (1H, m), 8.00-8.12 (1H, m), 8.32-8.44 (1H, m), 9.30-9.65 (1H, m); $^{13}$C NMR (100 MHz, CD$_3$OD) δ 11.05/11.48, 25.38/26.79/26.85/ 27., 34.98/35.21/35.46, 50.21/50.61/52.95/53.04/53.22/ 53.30, 60.06/60.40/60.46, 98.51/98.73/98.80, 106.19/ 106.46, 121.54, 121.84/121.92/121.99, 129.29/129.59, 131.04/131.31, 138.33, 139.50/139.58, 159.92/160.01, 170.28/170.40, 173.66.

Example 27

5-Fluoro-4-oxo-3-[(2S)-2-[1-(3-chlorobenzyl)-2-oxo-1,4-dihydro-2H-quinazolin-3-yl]-3-methyl-butyrylamino]-pentanoic acid (1D-1)

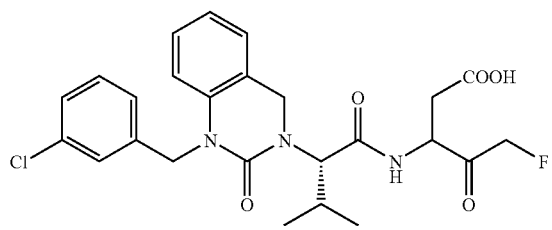

Step V: (2S)-3-Methyl-2-(2-nitro-benzylamino)-butyric acid tert-butyl ester

To a solution of valine tert-butyl ester hydrochloride (1.5 g, 7.15 mmol) in EtOH (10 mL) was added triethylamine (2.09 mL, 15 mmol), followed after 10 minutes by 2-nitrobenzyl chloride (1.227 g, 7.15 mmol). The mixture was then stirred for 20 h under reflux before it was evaporated. The residue was purified by flash chromatography (petrol/ethyl acetate, 85/15) to afford the sub-title compound as a colorless oil (1.753 g, 80%). $^1$H NMR (400 MHz CDCl$_3$) δ 0.93 (6H, m), 1.48 (9H, s), 1.83-1.96 (2H, m), 2.82 (1H, d), 3.92 (1H, d), 4.11 (1H, d), 7.39 (1H, t), 7.57 (1H, t), 7.65 (1H, d), 7.89 (1H, d).

Step W: (2S)-2-(2-amino-benzylamino)-3-Methyl-butyric acid tert-butyl ester

To a solution of (2S)-3-methyl-2-(2-nitro-benzylamino)-butyric acid tert-butyl ester (1.753 g, 5.68 mmol) in EtOH (30 mL) was added Raney nickel (1.3 mL) and the reaction mixture was hydrogenated under balloon pressure for 2 hours. The catalyst was filtrated and the filtrate evaporated to give the sub-title compound as a yellow oil (1.573 g, 100%). $^1$H NMR (400 MHz CDCl$_3$) δ 0.81-0.90 (6H, m), 1.55 (9H, s), 1.90 (1H, m), 2.89 (1H, d), 3.62 (1H, d), 3.86 (1H, d), 4.68 (2H, vbr s), 6.68 (2H, m), 7.02 (1H, d), 7.13 (1H, t).

Step X: (2S)-3-Methyl-2-(2-oxo-1,4-dihydro-2H-quinazolin-3-yl)-butyric acid tert-butyl ester To a solution of (2S)-2-(2-amino-benzylamino)-3-methyl-butyric acid tert-butyl ester (1.573 g, 5.65 mmol) in THF (20 mL) was added carbonyldiimidazol (1.008 g, 6.21 mmol) and the reaction was stirred under reflux overnight. The solvent was evaporated and the residue purified by flash chromatography (hexane/ethyl acetate, 50/50) to afford the sub-title compound as a yellow solid (662 mg, 38%). $^1$H NMR (400 MHz CDCl$_3$) δ 0.95 (3H, d), 1.08 (3H, d), 1.49 (9H, s), 2.32 (1H, m), 4.39 (1H, d), 4.60 (1H, d), 4.72 (1H, d), 6.81 (1H, d), 6.94 (1H, t), 7.07 (1H, d), 7.18 (1H, t), 8.68 (1H, s).

Step Y: (2S)-2-[1-(3-chloro-benzyl)-2-oxo-1,4-dihydro-2H-quinazolin-3-yl]-3-Methyl-butyric acid tert-butyl ester To a mixture of (2S)-3-methyl-2-(2-oxo-1,4-dihydro-2H-quinazolin-3-yl)-butyric acid tert-butyl ester (633 mg, 2.08 mmol) and 3-chlorobenzyl bromide (470 mg, 2.29 mmol) in DMSO (10 mL) was added sodium hydride (75 mg, 1.87 mmol) and the reaction mixture was stirred at room temperature for 40 hours. To this reaction was then added sat. aq. NH$_4$Cl and the mixture was extracted with ethyl acetate. The organic phase was dried (MgSO$_4$), filtered and evaporated. The residue was purified by flash chromatography (hexane/ ethyl acetate, 70/30) to afford the title compound as a colorless oil (477 mg, 59%). $^1$H NMR (400 MHz CDCl$_3$) δ 0.99 (3H, d), 1.08 (3H, d), 1.48 (9H, s), 2.32 (1H, m), 4.42 (1H, d), 4.59-4.67 (2H, m), 5.05-5.19 (2H, m), 6.68 (1H, d), 6.97 (1H, t), 7.06-7.27 (6H, m).

5-Fluoro-4-oxo-3-[(2S)-2-[1-(3-chlorobenzyl)-2-oxo-1, 4-dihydro-2H-quinazolin-3-yl]-3-methyl-butyrylamino]-pentanoic acid was prepared from the above compound using procedures similar to those described in step O and then C-E. IR (solid) 1736, 1365, 1227, 1217, 1203 cm$^{-1}$; $^1$H NMR (400 MHz, DMSO-d$_6$) δ 0.84-0.97 (6H, m), 2.30-2.33 (1H, m), 2.54-2.87 (2H, m), 4.39-5.24 (8H, m), 6.73-6.78 (1H, m), 6.93-6.97 (1H, m), 7.11-7.35 (6H, m), 8.21-8.76 (1H, m); $^{19}$F NMR (376 MHz, DMSO-d$_6$) δ −232.2 (t), −232.8 (t); $^{13}$C NMR (100 MHz, DMSO-d$_6$) δ 19.4/19.5, 26.1/26.4, 34.6/ 34.8, 43.8, 45.6/45.7, 51.8/52.0, 62.7/63.1, 84.1/84.3, 113.6, 121.3/121.4, 122.4/122.5, 125.3, 126.1, 126.6, 127.1, 128.2, 130.7, 133.5, 137.9/138.0, 141.0/141.0, 155.5/155.7, 170.8, 172.0/172.0, 202.6/202.9.

The compounds of this invention are designed to inhibit caspases. Therefore, the compounds of this invention can be assayed for their ability to inhibit apoptosis, the release of IL-1β or caspase activity directly. Assays for each of the activities are known in the art and are described below in detail in the Testing section.

According to another embodiment, the invention provides a composition comprising a compound of this invention or a pharmaceutically acceptable salt thereof, as described above, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal chord injury, hepatitis-B, hepatitis-C, hepatitis-G, yellow fever, dengue fever, or Japanese encephalitis, various forms of liver disease, renal disease, polycystic kidney disease, *H. pylori*-associated gastric and duodenal ulcer disease, HIV infection, tuberculosis, and meningitis. The compounds and compositions are also useful in treating complications associated with coronary artery bypass grafts. The amount of compound present in the above-described compositions should be sufficient to cause a detectable decrease in the severity of the disease or in caspase activity and/or cell apoptosis, as measured by any of the assays described in the examples.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

Example 28

Enzyme Assays

The assays for caspase inhibition are based on the cleavage of a fluorogenic substrate by recombinant, purified human Caspases-1, -3, -7 or -8. The assays are run in essentially the same way as those reported by Garcia-Calvo et al. (J. Biol. Chem. 273 (1998), 32608-32613), using a substrate specific for each enzyme. The substrate for Caspase-1 is Acetyl-Tyr-Val-Ala-Asp-amino-4-methylcoumarin. The substrate for Caspases-3, -7 and -8 is Acetyl-Asp-Glu-Val-Asp-amino-4-methylcoumarin.

The observed rate of enzyme inactivation at a particular inhibitor concentration, $k_{obs}$, is computed by direct fits of the data to the equation derived by Thornberry et al. (Biochemistry 33 (1994), 3943-3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression.

Table 8 shows inhibition of caspase-1 activity for selected compounds of this invention as determined by the above method.

TABLE 8

| Caspase-1 Activity | |
| --- | --- |
| Compound Number | Kinact ($M^{-1}s^{-1}$) |
| 1A-3 | 36000 |
| 1A-4 | 40000 |

TABLE 8-continued

Caspase-1 Activity

| Compound Number | Kinact (M$^{-1}$s$^{-1}$) |
|---|---|
| 1B-1 | 47000 |
| 1C-1 | 248000 |
| 1C-11 | 419000 |
| 1D-1 | 107000 |
| 1E-1 | 46000 |
| 1F-3 | 115000 |
| 1G-1 | 307000 |

Table 9 shows inhibition of caspase-3 activity for selected compounds of this invention as determined by the above method.

TABLE 9

Caspase-3 Activity

| Compound Number | Kinact (M$^{-1}$s$^{-1}$) |
|---|---|
| 1A-3 | 51000 |
| 1A-4 | — |
| 1B-1 | 24000 |
| 1C-1 | 130000 |
| 1C-11 | 185000 |
| 1D-1 | 67000 |
| 1E-1 | 64000 |
| 1F-3 | 220000 |
| 1G-1 | 420000 |

Table 10 shows inhibition of caspase-7 and -8 activity for selected compounds of this invention as determined by the above methods.

TABLE 10

Caspase-7 and -8 Activity

| Compound Number | Caspase-7 Kinact (M$^{-1}$s$^{-1}$) | Caspase-8 Kinact (M$^{-1}$s$^{-1}$) |
|---|---|---|
| 1A-3 | — | 6750 |
| 1A-4 | — | 13500 |
| 1B-1 | — | 12000 |
| 1C-1 | 26000 | 27000 |
| 1C-11 | — | 72500 |
| 1D-1 | — | 77000 |
| 1E-1 | — | 13500 |
| 1F-3 | — | 15500 |
| 1G-1 | 147000 | 68500 |

Example 29

Inhibition of IL-1β Secretion from Mixed Population of Peripheral Blood Mononuclear Cells (PBMC)

Processing of pre-IL-1β by caspase-1 can be measured in cell culture using a variety of cell sources. Human PBMC obtained from healthy donors provides a mixed population of lymphocyte and mononuclear cells that produce a spectrum of interleukins and cytokines in response to many classes of physiological stimulators.

Experimental Procedure

The test compound is dissolved in dimethyl sulfoxide (DMSO, Sigma #D-2650) to give a 100 mM stock solution. This is diluted in complete medium consisting of RPMI containing 10% heat inactivated FCS (Gibco BRL #10099-141), 2 mM L-Glutamine (Sigma, #G-7513), 100 U penicillin and 100 µg/ml streptomycin (Sigma #P-7539). The final concentration range of test compound is from 100 µM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17-1440-02) and the cellular assay is performed in a sterile 96 well flat-bottomed plate (Nunc). Each well contains 100 µl of the cell suspension, 1×10$^5$ cells, 50 µl of compound dilutions and 50 µl of LPS (Sigma #L-3012) at 50 ng/ml final concentration. Controls consist of cells+/−LPS stimulation and a serial dilution of DMSO diluted in the same way as compound. The plates are incubated for 16-18 h at 37° C. in 5% CO$_2$ & 95% humidity atmosphere.

After 16-18 h the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600-1500 pg/ml are observed for PBMCs in positive control wells.

The inhibitory potency of the compounds can be represented by an IC$_{50}$ value, which is the concentration of inhibitor at which 50% of the mature IL-1β is detected in the supernatant as compared to the positive controls. Table 11 shows inhibition of IL-1β secretion from peripheral blood mononuclear cells for selected compounds of this invention as determined by the above methods.

TABLE 11

Inhibition of IL-1β secretion from PBMC

| Compound Number | IC$_{50}$ (µM) |
|---|---|
| 1A-3 | — |
| 1A-4 | — |
| 1B-1 | — |
| 1C-1 | 2.9 |
| 1C-11 | 0.4 |
| 1D-1 | — |
| 1E-1 | 10.0 |
| 1F-3 | 4.0 |
| 1G-1 | 0.6 |

Example 30

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No. 10099-141)+2 mM L-glutamine (Sigma No. G-7513). The cells are harvested in log phase of growth. 100 ml Cells at 5-8×10$^5$ cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to 2×10$^6$ cells/ml with complete medium.

The test compound is dissolved in dimethyl sulphoxide (DMSO) (Sigma No. D-2650) to give a 100 mM stock solution. This is diluted to 400 µM in complete medium, then serially diluted in a 96-well plate prior to addition to the cell assay plate.

100 µl of the cell suspension (2×10$^6$ cells) is added to each well of a sterile 96-well round-bottomed cluster plate (Costar No. 3790). 50 µl of compound solution at the appropriate dilution and 50 µl of anti-Fas antibody, clone CH-11 (Kamiya No. MC-060) at a final concentration of 10 ng/ml, are added to the wells. Control wells are set up minus antibody and minus compound but with a serial dilution of DMSO as vehicle control. The plates are incubated for 16-18 hrs at 37° C. in 5% CO$_2$ and 95% humidity.

Apoptosis of the cells is measured by the quantitation of DNA fragmentation using a 'Cell Death Detection Assay' from Boehringer-Mannheim, No. 1544 675. After incubation for 16-18 hrs the assay plates are centrifuged at 100×g at room temperature for 5 minutes. 150 µl of the supernatant are removed and replaced by 150 µl of fresh complete medium. The cells are then harvested and 200 µl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 µl of this solution is then assayed exactly according to the manufacturer's instructions supplied with the kit. OD$_{405}$ nm is measured 20 minutes after addition of the final substrate in a SPECTRAmax Plus plate reader (Molecular Devices). OD$_{405}$ nm is plotted versus compound concentration and the IC$_{50}$ values for the compounds are calculated using the curve fitting program SOFTmax Pro (Molecular Devices) using the four parameter fit option.

Table 12 shows the results of the activity of selected compounds of this invention in the FAS induced apoptosis assay.

TABLE 12

Activity in FAS Induced Apoptosis Assay

| Compound Number | IC$_{50}$ (µM) |
|---|---|
| 1A-3 | 0.21 |
| 1A-4 | 0.65 |
| 1B-1 | 0.14 |
| 1C-1 | 0.06 |
| 1C-11 | 0.02 |
| 1D-1 | 0.02 |
| 1E-1 | 0.07 |
| 1F-3 | 0.03 |
| 1G-1 | 0.02 |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example

We claim:

1. A compound of formula IE:

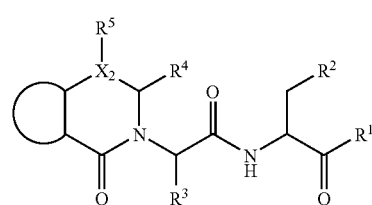

where R$^1$ is hydrogen, CN, CHN$_2$, R, —CH$_2$Y;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or —OR, —SR, —OC=O(R), or —OPO(R$^8$)(R$^9$);

R$^8$ and R$^9$ are independently selected from R or OR;

R$^2$ is CO$_2$H, CH$_2$CO$_2$H, or esters or isosteres thereof;

R$^3$ is hydrogen or a C$_{1-6}$ straight chained or branched alkyl;

R$^4$ and R$^5$ are each independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R;

X$_2$ is carbon;

the bond between X$_2$ and the adjacent CR$_4$ is either a double or single bond; and the fused ring is an aromatic or non-aromatic heterocyclic ring.

2. The compound of claim 1 where R$^2$ is CO$_2$H or an ester, amide or carboxylic acid isoster.

3. The compound of claim 1 where R$^1$ is CH$_2$Y and Y is F, OR, SR, or —OC=O(R).

4. The compound of claim 1 where R$^3$ is hydrogen or C$_{1-3}$ alkyl.

5. The compound of claim 1 where R$^1$ is CH$_2$Y and Y is F, —OR, —SR, —OC=O(R), R$^2$ is CO$_2$H and esters, amides or isosters thereof, R$^3$ is H or C$_{1-3}$ alkyl, and the fused ring is a five or six membered heterocycle having one ring heteroatom.

6. A compound selected from those listed in Table 5 below:

TABLE 5

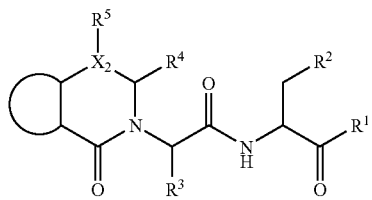

R$^1$ is CH$_2$F; R$^2$ is CO$_2$H;

| No. | Heterocycle | R$^3$ | R$^4$ | R$^5$ | X$_2$ | Bond order X$^2$—CR$^4$ |
|---|---|---|---|---|---|---|
| IE-2 | Pyridine[4,3-d] | H | H | H | C | double |

7. A pharmaceutical composition comprising: a) a compound according to claim 1; and b) a pharmaceutically acceptable carrier, adjuvant or vehicle.

8. A method of preparing a compound of formula IE,

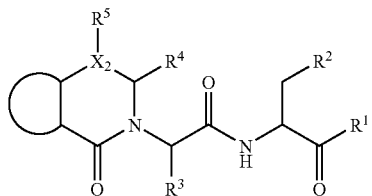

said method comprising the steps of:

(a) providing an acid or acid derivative of formula II,

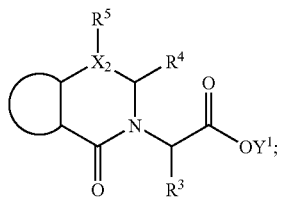

(b) coupling II with an amino alcohol or amino ketone of formula 4 to provide an intermediate of formula III,

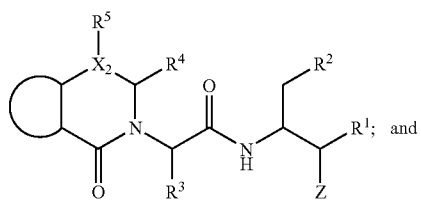

(c) converting intermediate III to compound IE, wherein $Y^1$ is hydrogen or an organic radical;

Z is =O or OH;

$X_2$ is carbon; the bond between $X_2$ and the adjacent $CR_4$ is either a double or single bond;

$R^1$ is hydrogen, CN, $CHN_2$, R, —$CH_2Y$;

R is an aliphatic group, a substituted aliphatic group, an aryl group, a substituted aryl group, an aralkyl group, a substituted aralkyl group, a non-aromatic heterocyclic group or a substituted non-aromatic heterocyclic group;

Y is an electronegative leaving group or —OR, —SR, —OC=O(R), or —OPO($R^8$)($R^9$);

$R^8$ and $R^9$ are independently selected from R or OR;

$R^2$ is $CO_2H$, $CH_2CO_2H$, or esters or isosteres thereof;

$R^3$ is hydrogen or a $C_{1-6}$ straight chained or branched alkyl;

$R^4$ and $R^5$ are each independently selected from hydrogen, halo, R, OR, SR, aryl, substituted aryl, OH, $NO_2$, CN, $NH_2$, NHR, N(R)$_2$, NHCOR, NHCONHR, NHCON(R)$_2$, NRCOR, $NHCO_2R$, $CO_2R$, $CO_2H$, COR, CONHR, CON(R)$_2$, S(O)$_2R$, $SONH_2$, S(O)R, $SO_2NHR$, or NHS(O)$_2R$; and the fused ring is an aromatic or non-aromatic heterocyclic ring.

* * * * *